(12) United States Patent
Schepis et al.

(10) Patent No.: US 11,464,971 B2
(45) Date of Patent: Oct. 11, 2022

(54) SELECTIVE NERVE FIBER BLOCK METHOD AND SYSTEM

(71) Applicant: Avent, Inc., Alpharetta, GA (US)

(72) Inventors: Eric A. Schepis, Alpharetta, GA (US); Phillip A. Schorr, Cumming, GA (US); Jeremy D. Ollerenshaw, Alpharetta, GA (US); Roger D. Massengale, Alpharetta, GA (US); Joshua D. White, Atlanta, GA (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 15/501,450

(22) PCT Filed: Aug. 24, 2015

(86) PCT No.: PCT/US2015/046482
§ 371 (c)(1),
(2) Date: Feb. 3, 2017

(87) PCT Pub. No.: WO2016/032929
PCT Pub. Date: Mar. 3, 2016

(65) Prior Publication Data
US 2017/0224989 A1 Aug. 10, 2017

Related U.S. Application Data

(60) Provisional application No. 62/041,774, filed on Aug. 26, 2014.

(51) Int. Cl.
*A61N 1/36* (2006.01)
*A61N 1/05* (2006.01)

(52) U.S. Cl.
CPC ....... *A61N 1/36021* (2013.01); *A61N 1/0553* (2013.01); *A61N 1/0556* (2013.01); *A61N 1/36057* (2013.01); *A61N 1/36071* (2013.01)

(58) Field of Classification Search
CPC ............ A61N 1/36021; A61N 1/36071; A61N 1/36139
See application file for complete search history.

(56) References Cited

U.S. PATENT DOCUMENTS

| 5,344,438 A | 9/1994 | Testerman et al. |
| 5,755,750 A | 5/1998 | Petruska et al. |

(Continued)

FOREIGN PATENT DOCUMENTS

| WO | 2006029257 | 3/2006 |
| WO | 2008/106174 | 9/2008 |

(Continued)

OTHER PUBLICATIONS

Joseph et al., "High-Frequency Stimulation Selectively Blocks Different Types of Fibers in Frog Sciatic Nerve", IEEE Transactions on Neural Systems and Rehabilitation Engineering, vol. 19, No. 5, Oct. 5, 2011, 8 pages.

(Continued)

*Primary Examiner* — William J Levicky
(74) *Attorney, Agent, or Firm* — Meunier Carlin & Curfman LLC

(57) ABSTRACT

A system for selectively blocking nerve fiber activity in a target nerve is provided. The system includes one or more electrodes. The system further includes an electronic control system electrically attached to each electrode to deliver electrical stimulation to a target nerve to block nerve signal transmission of C-fibers in the target nerve such that the nerve signal transmission of A-fibers in the target nerve providing motor function and/or low-threshold sensory function is not blocked. A method of delivering electrical stimulation to selectively block nerve fiber activity in a target nerve and a kit for performing a procedure to selectively block nerve fiber activity are disclosed.

30 Claims, 9 Drawing Sheets

(56) References Cited

U.S. PATENT DOCUMENTS

| | | |
|---|---|---|
| 6,319,241 B1 | 11/2001 | King et al. |
| 6,602,248 B1 | 8/2003 | Sharps et al. |
| 6,981,967 B2 | 1/2006 | Massengale et al. |
| 7,389,145 B2 | 6/2008 | Kilgore et al. |
| 7,403,821 B2 | 7/2008 | Haugland et al. |
| 8,027,718 B2 | 9/2011 | Spinner et al. |
| 8,060,208 B2 | 11/2011 | Kilgore et al. |
| 8,463,383 B2 | 6/2013 | Sakai et al. |
| 8,612,020 B2 | 12/2013 | Donofrio |
| 8,644,953 B1 | 2/2014 | Finley et al. |
| 8,700,177 B2 | 4/2014 | Strother et al. |
| 8,731,676 B2 | 5/2014 | Fang et al. |
| 8,751,009 B2 | 6/2014 | Wacnik |
| 8,774,913 B2 | 7/2014 | Demarais et al. |
| 8,843,188 B2 | 9/2014 | Kilgore et al. |
| 8,855,776 B2 | 10/2014 | Lin et al. |
| 8,965,516 B2 | 2/2015 | Bennett et al. |
| 8,983,612 B2 | 3/2015 | Fang et al. |
| 8,983,614 B2 | 3/2015 | Kilgore et al. |
| 9,008,800 B2 | 4/2015 | Ackermann, Jr. et al. |
| 9,037,248 B2 | 5/2015 | Durand et al. |
| 9,119,966 B2 | 9/2015 | Franke et al. |
| RE45,718 E | 10/2015 | Kilgore et al. |
| 9,205,258 B2 | 12/2015 | Simon et al. |
| 9,205,265 B2 | 12/2015 | Franke |
| 9,248,289 B2 | 2/2016 | Bennett et al. |
| 9,259,571 B2 | 2/2016 | Straka et al. |
| 9,259,578 B2 | 2/2016 | Torgerson |
| 9,295,841 B2 | 3/2016 | Fang et al. |
| 9,333,356 B2 | 5/2016 | Franke et al. |
| 9,339,647 B2 | 5/2016 | Strother et al. |
| 9,358,374 B2 | 6/2016 | Dacey, Jr. et al. |
| 9,364,661 B2 | 6/2016 | Kilgore et al. |
| 9,387,322 B2 | 7/2016 | Bhadra et al. |
| 9,403,014 B2 | 8/2016 | Kilgore et al. |
| 9,409,020 B2 | 8/2016 | Parker |
| 9,415,211 B2 | 8/2016 | Bradley et al. |
| 9,498,621 B2 | 11/2016 | Ackermann et al. |
| 9,555,245 B2 | 1/2017 | Boggs, II et al. |
| 9,566,426 B2 | 2/2017 | Simon et al. |
| 9,636,497 B2 | 5/2017 | Bradley et al. |
| 9,694,181 B2 | 7/2017 | Bhadra et al. |
| 9,707,394 B2 | 7/2017 | Bennett et al. |
| 9,884,192 B2 | 2/2018 | Kilgore et al. |
| 9,889,291 B2 | 2/2018 | Bhadra et al. |
| 10,039,917 B2 | 8/2018 | Kilgore et al. |
| 10,071,241 B2 | 9/2018 | Bhadra et al. |
| 10,195,434 B2 | 2/2019 | Bhadra et al. |
| 10,360,511 B2 | 7/2019 | Lujan et al. |
| 2001/0032001 A1 | 10/2001 | Ricart et al. |
| 2002/0120259 A1 | 8/2002 | Lettice et al. |
| 2003/0014047 A1 | 1/2003 | Wolosko et al. |
| 2003/0100924 A1 | 5/2003 | Foreman et al. |
| 2003/0158545 A1 | 8/2003 | Hovda et al. |
| 2003/0195602 A1 | 10/2003 | Boling |
| 2005/0177202 A1 | 8/2005 | Classen |
| 2005/0197678 A1* | 9/2005 | Boveja ............... A61N 1/36014 607/42 |
| 2005/0288730 A1 | 12/2005 | Deem |
| 2006/0184211 A1 | 8/2006 | Gaunt et al. |
| 2006/0200121 A1 | 9/2006 | Mowery |
| 2007/0191915 A1 | 8/2007 | Strother |
| 2008/0027505 A1 | 1/2008 | Levin et al. |
| 2008/0071321 A1 | 3/2008 | Boggs, II et al. |
| 2008/0132962 A1* | 6/2008 | DiUbaldi ........... A61N 1/36007 607/2 |
| 2008/0147155 A1 | 6/2008 | Swoyer et al. |
| 2008/0208287 A1 | 8/2008 | Palermo et al. |
| 2008/0294221 A1* | 11/2008 | Kilgore ............... A61N 1/36017 607/46 |
| 2009/0149926 A1 | 6/2009 | Dacey, Jr. et al. |
| 2009/0259279 A1* | 10/2009 | Dobak, III ......... A61N 1/36167 607/72 |
| 2010/0016929 A1 | 1/2010 | Prochazka |
| 2010/0152808 A1* | 6/2010 | Boggs, II ............ A61N 1/0456 607/46 |
| 2010/0191311 A1* | 7/2010 | Scheiner ............. A61N 1/0556 607/62 |
| 2010/0274318 A1* | 10/2010 | Walker ............... A61N 1/36071 607/46 |
| 2011/0159748 A1 | 6/2011 | Lim et al. |
| 2011/0224665 A1 | 9/2011 | Crosby et al. |
| 2011/0301670 A1 | 12/2011 | Gross |
| 2012/0046715 A1* | 2/2012 | Moffitt ............... A61N 1/36185 607/59 |
| 2012/0197372 A1 | 8/2012 | Burgher |
| 2012/0277823 A1* | 11/2012 | Gerber ............... A61N 1/36075 607/46 |
| 2012/0290031 A1 | 11/2012 | Bjorling et al. |
| 2012/0290053 A1* | 11/2012 | Zhang ................. A61N 1/0558 607/116 |
| 2012/0296389 A1 | 11/2012 | Fang et al. |
| 2012/0330218 A1 | 12/2012 | Bradley |
| 2013/0066393 A1 | 3/2013 | Gross et al. |
| 2013/0110194 A1 | 5/2013 | Wei |
| 2013/0116752 A1 | 5/2013 | Parker et al. |
| 2013/0138193 A1 | 5/2013 | Durand et al. |
| 2013/0238066 A1 | 9/2013 | Boggs, II et al. |
| 2013/0253299 A1 | 9/2013 | Weber et al. |
| 2013/0257625 A1 | 10/2013 | Holle |
| 2013/0261697 A1* | 10/2013 | Parker ................ A61N 1/36071 607/46 |
| 2013/0296966 A1 | 11/2013 | Wongsarnpigoon et al. |
| 2013/0317303 A1 | 11/2013 | Deshmukh et al. |
| 2014/0058495 A1 | 2/2014 | Sakai et al. |
| 2014/0135858 A1 | 5/2014 | Ahmed et al. |
| 2014/0148735 A1 | 5/2014 | Nau, Jr. |
| 2014/0148753 A1 | 5/2014 | Leven |
| 2014/0163660 A1* | 6/2014 | Fang ................... A61N 1/0551 607/117 |
| 2014/0324129 A1 | 10/2014 | Franke et al. |
| 2014/0343655 A1* | 11/2014 | Rao .................... A61N 1/36067 607/117 |
| 2014/0358191 A1 | 12/2014 | Kilgore et al. |
| 2015/0012063 A1 | 1/2015 | Chen |
| 2015/0100106 A1 | 4/2015 | Shishilla et al. |
| 2015/0105840 A1 | 4/2015 | Boggs |
| 2015/0127068 A1 | 5/2015 | Simon et al. |
| 2015/0148878 A1* | 5/2015 | Yoo .................... A61N 1/0456 607/118 |
| 2015/0174397 A1 | 6/2015 | Bhadra et al. |
| 2015/0182742 A1 | 7/2015 | Ackermann et al. |
| 2015/0238259 A1 | 8/2015 | Albeck et al. |
| 2015/0238764 A1 | 8/2015 | Franke |
| 2015/0320481 A1 | 11/2015 | Cosman |
| 2016/0030408 A1 | 2/2016 | Levin |
| 2016/0128767 A1 | 5/2016 | Azamian et al. |
| 2016/0213927 A1 | 7/2016 | Mcgee et al. |
| 2016/0235969 A1 | 8/2016 | Kilgore et al. |
| 2016/0331976 A1 | 11/2016 | Kilgore et al. |
| 2016/0339239 A1 | 11/2016 | Yoo et al. |
| 2016/0339241 A1 | 11/2016 | Hargrove et al. |
| 2017/0173329 A1 | 6/2017 | Boggs, II et al. |
| 2017/0197079 A1 | 7/2017 | Illegems et al. |
| 2017/0209695 A1 | 7/2017 | Solomon |
| 2017/0224989 A1 | 8/2017 | Schepis et al. |
| 2017/0246453 A1 | 8/2017 | Fang et al. |
| 2017/0312523 A1 | 11/2017 | Bennett et al. |
| 2018/0028804 A1 | 2/2018 | Pianca |
| 2018/0085587 A1 | 3/2018 | Kilgore et al. |
| 2018/0250506 A1 | 9/2018 | Kilgore et al. |
| 2018/0256886 A1 | 9/2018 | Bhadra et al. |
| 2018/0361155 A1 | 12/2018 | Bhadra et al. |
| 2019/0060640 A1 | 2/2019 | Bhadra et al. |
| 2019/0282267 A1 | 9/2019 | Caldwell et al. |
| 2019/0282799 A1 | 9/2019 | Schepis et al. |
| 2019/0282809 A1 | 9/2019 | Schepis et al. |

(56) References Cited

U.S. PATENT DOCUMENTS

2019/0282810 A1 9/2019 Schepis et al.
2019/0282814 A1 9/2019 Schepis et al.

FOREIGN PATENT DOCUMENTS

| WO | 2009/061813 | 5/2009 |
|---|---|---|
| WO | 2012021583 | 2/2012 |
| WO | 2012/159002 | 11/2012 |
| WO | 2014126718 | 8/2014 |
| WO | 2015/003561 | 1/2015 |
| WO | 2016/039768 | 3/2016 |
| WO | 2016/094728 | 6/2016 |
| WO | 2017/044542 | 3/2017 |
| WO | 2017/066734 | 4/2017 |
| WO | 2018/085611 | 5/2018 |

OTHER PUBLICATIONS

International Search Report and Written Opinion for PCT/US2015/046482, dated Mar. 22, 2016, 21 pages.

Kapural et al.; "Novel 10-kHz High-frequency Therapy (HF10 Therapy) Is Superior to Traditional Low-frequency Spinal Cord Stimulation for the Treatment of Chronic Back and Leg Pain"; Anesthesiology 2015, Dated: 2015; 11 pages.

Finch et al.; "High-Frequency (10 kHz) Electrical Stimulation of Peripheral Nerves for Treating Chronic Pain: A Double-Blind Trial of Presence vs Absence of Stimulation"; Neuromodulation 2018; Dated: 2018; 8 pages.

M.H. Lev, et al., CT Angiography and CT Perfusion Imaging. Brain Mapping: The Methods (2nd Ed.) 2002, 427-484.

Office Action issued for U.S. Appl. No. 16/355,660, dated Dec. 9, 2020.

Office Action issued for U.S. Appl. No. 16/355,660, dated Apr. 19, 2021.

Office Action issued for U.S. Appl. No. 16/355,660, dated Nov. 1, 2021.

Notice of Allowance issued for U.S. Appl. No. 16/355,670, dated Dec. 10, 2021.

Office action issued for U.S. Appl. No. 16/355,670, dated Jul. 14, 2021.

Franke, Manfred, et al. "Combined KHFAC+ DC nerve block without onset or reduced nerve conductivity after block." Journal of neural engineering 11.5 (2014): 056012.

Frahm, Ken Steffen, et al. "Nerve fiber activation during peripheral nerve field stimulation: importance of electrode orientation and estimation of area of paresthesia." Neuromodulation: Technology at the Neural Interface 19.3 (2016): 311-318.

Kilgore, Kevin L., and Niloy Bhadra. "Reversible nerve conduction block using kilohertz frequency alternating current." Neuromodulation: Technology at the Neural Interface 17.3 (2014): 242-255.

* cited by examiner

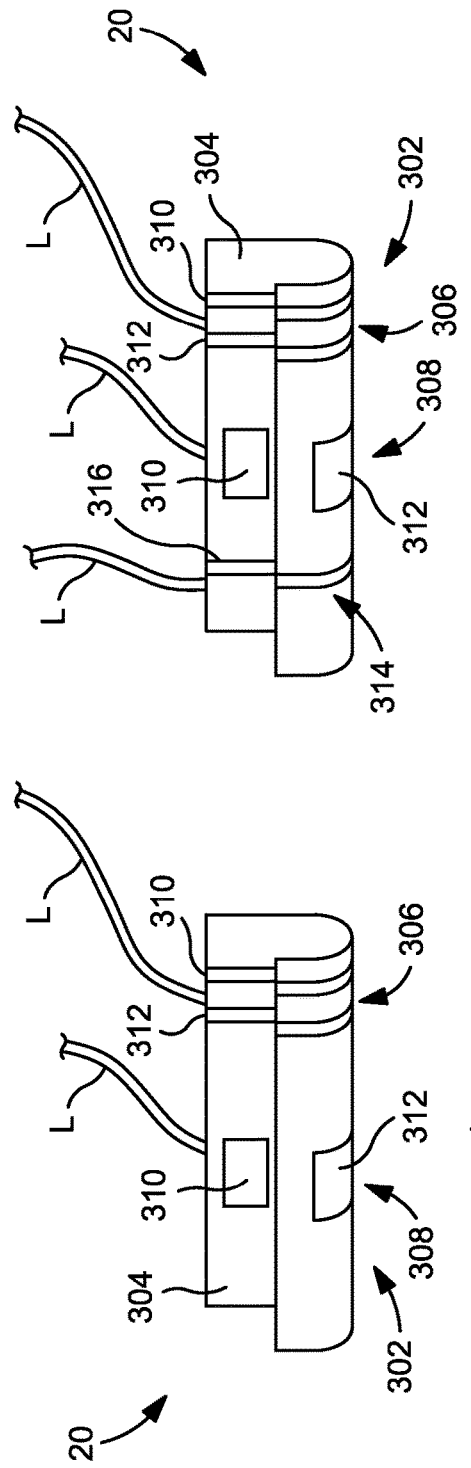
FIG. 2
FIG. 3
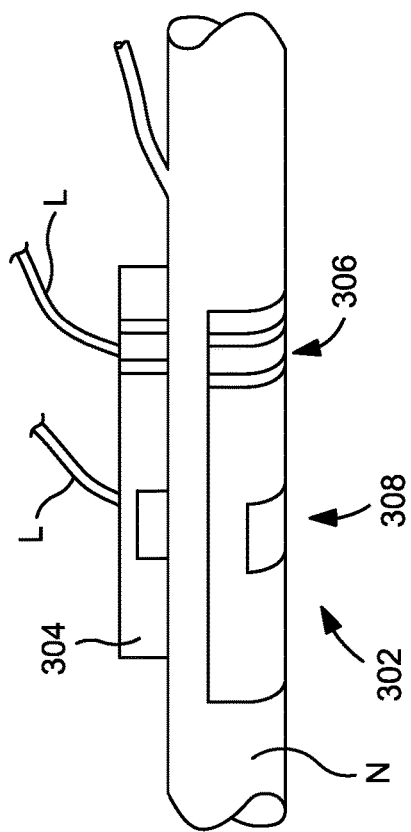
FIG. 4

SELECTIVE NERVE FIBER BLOCK METHOD AND SYSTEM

RELATED APPLICATIONS

This application is the national stage entry of International Patent Application No PCT/US2015/046482 having a filing date of Aug.24, 2015, which claims priority to U.S. Provisional Application No. 62/041,774, filed on Aug. 26, 2014, both of which are incorporated herein in their entirety by reference thereto.

The present application claims priority to U.S. Provisional Application No. 62/041,774, filed on Aug. 26, 2014, which is incorporated herein in its entirety by reference thereto.

The disclosure generally relates to a medical device and method for electrically blocking nerve signal transmission in a nerve.

BACKGROUND OF THE INVENTION

The general concept of stimulating nerves using electrical energy to block transmission of neural impulses is known in the art. Examples include a direct current (DC) block, often referred to as anodal block or galvanic block. Conventional DC stimulation provides an unbalanced charge that can damage nervous tissue, as well as the metal electrodes that are used to deliver it.

U.S. Pat. No. 5,755,750, issued May 26, 1998 to Petruska et al., for "Method and Apparatus for Selectively Inhibiting Activity in Nerve Fibers" observes that traditional electrophysiological stimulation uses a cathode and anode pair, and that the positive potential generated by the cathode stimulates peripheral nerve fibers of appropriate diameters (large fibers first by weaker stimulations, then progressively smaller axons with increasingly stronger stimulations). That patent also observes that evidence concerning the relationship of blocking threshold to fiber size shows that it tends to be more hyperbolic than linear and that such a relationship might strongly favor the ability to block conduction in the larger fibers while still allowing conduction in the smaller ones. Petruska et al. describe the use of a polarizing direct current (DC) waveform to carry out the block. Unfortunately, DC must be carefully controlled to avoid permanent damage to nerves.

In "High Frequency Stimulation Selectively Blocks Different Types of Fibers in Frog Sciatic Nerve", IEEE Transactions on Neural Systems and Rehabilitation Engineering, Vol. 19, No. 5, October 2011, L. Joseph and R. J. Butera; the authors observe that high frequency alternating current waveforms have a monotonic relationship between frequency and blocking thresholds for C-fibers and a non-monotonic relationship between frequency and blocking thresholds for A-fibers. The authors also observe that the ability to block smaller diameter unmyelinated pain fibers while allowing conduction through larger diameter myelinated fibers might provide a unique way to achieve a selective block.

While these references discuss that it might be possible to selectively block nerve fibers, they do not provide a practical, reliable and effective method and device for doing so. For example, these references demonstrate that electrical stimulation of nerve fibers may not provide consistent and predictable results and that many different factors can influence the outcome of electrical stimulation when attempting to selective block some nerve fibers and not others. Accordingly, there is a need for a method and system to carry out a selective nerve block without damaging nervous tissue.

The need extends to a method and system that can carry out a selective nerve block without causing painful sensations, or unwanted reflexive activity. There is also a need for a method and system to carry out a selective nerve block in a way that is reliable and effective. For example, there is a need for a method to carry out a selective nerve block utilizing a nerve cuff or collar that can directly deliver electrical stimulation to carry out the selective block of the target nerve by positioning the electrode substantially on, around, or adjacent the target nerve.

There is a need for a practical and effective system or apparatus for delivering electrical-nerve blocking stimulation percutaneously to carry out the selective block of the target nerve. A percutaneous application describes an electrode that may be introduced through a needle-puncture at the skin and positioned at the appropriate stimulation site within the body to affect an intended nerve. Desirably, the practical and effective system would be capable of selectively blocking a desired nerve without causing painful sensations. Additionally, the practical and effective system would be capable of selectively blocking a desired nerve without causing unwanted muscle contractions and/or blocking non-targeted nerves. There is also a need for a practical and effective method for delivering electrical-nerve blocking stimulation percutaneously to carry out the selective block of the target nerve.

There is a need for a practical and effective system or apparatus for delivering electrical-nerve blocking stimulation transcutaneously through the skin to carry out the selective block of the target nerve. Desirably, the practical and effective system would be capable of selectively blocking a desired nerve without causing painful sensations. Additionally, the practical and effective system would be capable of selectively blocking a desired nerve without causing unwanted muscle contractions and/or blocking non-targeted nerves. There is also a need for a practical and effective method for delivering electrical-nerve blocking stimulation transcutaneously through the skin to carry out the selective block of the target nerve.

BRIEF SUMMARY OF THE INVENTION

The problems described above are addressed by the present invention which encompasses systems and methods for selectively blocking nerve fiber activity. In particular, the nerve fiber activity blocked by the systems and methods of the present invention can occur in peripheral nerves, meaning those nerves that are not a part of the central nervous system, where such peripheral nerves include motor and sensory nerves that connect the brain and spinal cord to the rest of the body. An exemplary method includes the steps of identifying a target nerve and delivering electrical stimulation to the target nerve to block nerve signal transmission of C-fibers in the target nerve such that the nerve signal transmission of the A-fibers in the target nerve providing motor function and/or low-threshold sensory function is not blocked. In an aspect of the invention, the step of delivering electrical stimulation to the target nerve involves first delivering electrical stimulation to the target nerve to block nerve signal transmission of both A-fibers and C-fibers in the target nerve and then changing the amplitude and/or the frequency and/or the waveform of the electrical stimulation so nerve signal transmission of the C-fibers in the target nerve is blocked and so the nerve signal transmission of the A-fibers in the target nerve providing motor function and/or low-threshold sensory function is not blocked. The electrical stimulation in the practice of the present invention is desirably an alternating current and, more desirably, a charge-balanced high frequency alternating current.

According to an aspect of the invention, the method may involve the steps of identifying a target nerve; delivering an electrical stimulation at an initial frequency and amplitude to the target nerve; determining an electrical stimulation frequency and/or amplitude threshold sufficient to block nerve signal transmission in only one of A-fibers or C-fibers in the target nerve; and then delivering electrical stimulation to the target nerve at a frequency and amplitude to block nerve signal transmission of C-fibers in the target nerve such that the nerve signal transmission of the A-fibers in the target nerve providing motor function and/or low-threshold sensory function is not blocked.

According to an aspect of the invention, the step of delivering electrical stimulation to the target nerve may be carried out by positioning an electrode assembly substantially on, around or adjacent the target nerve and delivering the electrical stimulation to the target nerve at frequencies greater than about 30 kilohertz and at amplitudes of less than about 25 milliamps. More desirably, the electrical stimulation is delivered to the target nerve at frequencies of from about 30 kilohertz to about 100 kilohertz and amplitudes from about 0.5 milliamps to about 15 milliamps. For example, the electrical stimulation is delivered to the target nerve at frequencies of from about 30 kilohertz to about 75 kilohertz and amplitudes from about 0.5 milliamps to about 10 milliamps.

The electrode may be an electrode assembly in the form of a nerve cuff, collar or the like, and introduced in an open surgical fashion. The cuff includes at least a blocking electrode to contact the target nerve and may further include a stimulating electrode(s) located on the cuff. Desirably, the blocking electrode contacts the target nerve orthodromic to the stimulating electrode. The electrodes used for stimulation and/or blocking may be operated in a monopolar and/or multipolar fashion. Monopolar stimulation and/or blocking require a return electrode be placed at some distance from the cathode electrode. Preferably, stimulation and/or blocking will be delivered in a bipolar or multipolar fashion, where each electrode ensemble has an anode region for contacting the target nerve and a cathode region for contacting the target nerve. The nerve cuff may further include a recording electrode ensemble located on the cuff. Desirably, the recording electrode ensemble is configured to contact the target nerve orthodromic to the blocking electrode, the recording electrode ensemble having an active electrode for contacting the target nerve, an indifferent electrode and a reference electrode. It is contemplated that the recording electrode ensemble may utilize as few as two electrodes or the recording electrode ensemble may utilize more electrodes to stabilize the recorded signal. In an aspect of the invention, a local anesthetic may be applied to the target nerve prior to delivery of the electrical stimulation, the local anesthetic being applied in an amount sufficient to relieve an onset response in connection with the delivery of electrical stimulation used to block nerve signal transmission.

In another aspect of the invention, the delivery of electrical stimulation to the target nerve is carried out utilizing an electrode assembly in the form of a paddle, cylindrical catheter or needle, wire form, thin probe or the like, that is introduced percutaneously to deliver electrical stimulation to the target nerve at frequencies greater than about 30 kilohertz and amplitudes less than about 50 milliamps. For example, the frequencies may be from about 30 kilohertz up to about 200 kilohertz and the amplitudes may be from about 25 milliamps to about 0.5 milliamps. While the percutaneous electrode will be positioned so it is in electrical communication with the target nerve and may physically contact the target nerve, it is desirable that the percutaneous electrode avoid direct contact with the target nerve. For example, the electrode may be within 2 cm of the target nerve. As another example, the electrode may be within 1 cm of the target nerve. The percutaneous electrode assembly includes a blocking electrode(s) ensemble. The blocking electrode ensemble may be operated in a monopolar or multipolar fashion. The electrode ensemble used for monopolar blocking may include a single cathode electrode and have a return electrode some distance from the blocking site. The blocking electrode ensemble used in a bipolar or multipolar fashion has an anodal and cathodic region for affecting the target nerve. In an aspect of the invention, a local anesthetic may be applied to the target nerve prior to delivery of the electrical stimulation used to block nerve signal transmission, the local anesthetic being applied in an amount sufficient to relieve an onset response in connection with the delivery of electrical stimulation used to block nerve signal transmission.

The percutaneous electrode may define a lumen or passageway through the electrode to channel a fluid through the electrode and may further define openings in communication with the lumen or passageway to deliver fluid out through the electrode. Desirably, the electrode assembly defines openings adjacent the anode and cathode. The electrode assembly may be connected to a fluid flow path in communication with a source of fluid such as, for example, a syringe and/or a fluid pump, the fluid flow path configured to deliver a fluid to be dispensed to a patient through the electrode assembly. Alternatively and/or additionally, the electrode assembly may be connected to: a bolus reservoir in communication with a bolus flow path, the bolus reservoir configured to selectively permit fluid to be dispensed to a patient through the electrode assembly; and a patient operable actuator configured to dispense fluid from the bolus reservoir. It is contemplated that the bolus reservoir may be in the form of a syringe as well as other forms such as conventional bolus reservoirs used with infusion pumps. In such configurations, the percutaneous electrode can be used to delivery medicinal fluid such as liquid anesthetic in addition to nerve blocking electrical stimulation. The medicinal liquid may be a bolus of anesthetic or it may be an antibiotic material, antimicrobial material or an electrolytic solution to enhance delivery of electrical stimulation. If the medicinal liquid is or includes an electrolytic solution, the electrolytic solution may be or may include a bioresorbable gel material that is injected in liquid form but becomes substantially viscous or even solid-like after exiting the openings in the percutaneous electrode. Lastly, the viscous and form filling nature of the electrolytic solution may be used to better stabilize or anchor the electrode in position to reduce migration.

In another aspect of the invention, the step of delivering electrical stimulation to the target nerve is carried out by positioning one or more electrodes on the intact skin over the target nerve and delivering the electrical stimulation to the target nerve through the intact skin at frequencies greater than about 30 kilohertz and amplitudes less than about 50 milliamps. For example, the frequencies may be from about 30 kilohertz up to about 200 kilohertz and the amplitudes may be from about 25 milliamps to about 0.5 milliamps. In an embodiment, the electrode may be selected to provide the optimal stimulation depth, selectivity and/or avoidance of painful sensations. For example, a conventional TENS electrode may be utilized. In other embodiments, each electrode may have a generally uniform skin contacting surface area of from about 1.5 mm$^2$ to about 100 mm$^2$. Desirably, each electrode defines a generally uniform skin contacting surface having an area of from about 3.5 mm$^2$ to about 40 mm$^2$. According to the invention, these electrodes selectively block nerve signal transmission in the target nerve underlying the one or more electrodes without eliciting a painful sensation.

In an aspect of the invention, the electrical stimulation delivered by a percutaneous electrode and/or a transcutaneous electrode may further include a carrier frequency ranging from about 5 kilohertz to about 1 megahertz such that the carrier frequency is greater than the frequency of the electrical stimulation used to block nerve signal transmission. The present invention encompasses systems for selectively blocking nerve fiber activity. For example, a system for practicing the above described method includes one or more electrodes and an electronic control system electrically attached to each electrode—in which the electronic control system delivers electrical stimulation to a target nerve to block nerve signal transmission of C-fibers in the target nerve such that the nerve signal transmission of A-fibers in the target nerve providing motor function and/or low-threshold sensory function is not blocked. According to an aspect of the invention, the electronic control system may first provide electrical stimulation to the target nerve utilizing the one or more electrodes at a frequency and/or amplitude and/or waveform to block nerve signal transmission of both A-fibers and C-fibers in the target nerve, and then changing the amplitude, frequency and/or waveform of the electrical stimulation so nerve signal transmission of the C-fibers in the target nerve is blocked and so the nerve signal transmission of the A-fibers in the target nerve providing motor function and/or low-threshold sensory function is not blocked. In another aspect of the system, the electronic control system may first deliver electrical stimulation to the target at an amplitude and/or the frequency and/or waveform that does not block nerve signal transmission of both A-fibers and C-fibers in the target nerve and then changes the amplitude and/or the frequency and/or waveform of the electrical stimulation so nerve signal transmission of the C-fibers in the target nerve is blocked and so the nerve signal transmission of the A-fibers in the target nerve providing motor function and/or low-threshold sensory function is not blocked.

According to an aspect of the system invention, the electrodes may have one or more electrode assemblies to deliver electrical energy to a target nerve by way of a nerve cuff, nerve collar or nerve hook; desirably at frequencies greater than about 30 kilohertz and at amplitudes less than about 25 milliamps. For example, the frequencies may range from about 30 kilohertz to about 100 kilohertz and the amplitudes may range from about 0.5 milliamps to about 15 milliamps. For example, the electrical stimulation is delivered to the target nerve at frequencies of from about 30 kilohertz to about 75 kilohertz and amplitudes from about 0.5 milliamps to about 10 milliamps. Desirably, the one or more electrode assemblies may include a nerve cuff or collar having a stimulating electrode ensemble and a blocking electrode ensemble located on the cuff to contact the target nerve orthodromic to the stimulating electrode. The electrodes used for stimulation and/or blocking may be operated in a monopolar and/or multipolar fashion. Monopolar stimulation and/or blocking require a return electrode be placed at some distance from the cathode electrode. Preferably, stimulation and/or blocking will be delivered in a bipolar or multipolar fashion, where each electrode ensemble has an anode region for contacting the target nerve and a cathode region for contacting the target nerve. Each electrode may have an anode region for contacting the target nerve and a cathode region for contacting the target nerve. The nerve cuff may further include a recording electrode ensemble located on the cuff to contact the target nerve orthodromic to the blocking electrode. The recording electrode may have an active electrode for contacting the target nerve, an indifferent electrode and a reference electrode.

According to an aspect of the system invention, the electrodes may be in the form of one or more percutaneous electrode ensemble configurations to deliver electrical energy percutaneously to a target nerve by way of a paddle, cylindrical catheter or needle, wire form or the like; desirably at frequencies greater than about 30 kilohertz and at amplitudes less than about 25 milliamps. For example, the frequencies may range from about 30 kilohertz to about 100 kilohertz and the amplitudes may range from about 0.5 milliamps to about 25 milliamps. As another example, the frequencies may range from about 30 kilohertz to about 75 kilohertz and the amplitudes may range from about 0.5 milliamps to about 15 milliamps. Desirably, the one or more electrode ensembles for percutaneous blocking may be monopolar, bipolar or multipolar, and may include one, two, three or more electrodes that are placed in the vicinity of the nerve. Each electrode ensemble has a cathode region. Monopolar configurations have a return electrode placed some distance away, and may be a sticky electrode placed on the patient's skin. Bipolar and multipolar electrode configurations have at least one cathode and one anode in the vicinity of the nerve. The electrode shape and size, and inter-electrode spacing(s) are specific to contouring the electrical field surrounding the nerve, to enable selective blocking. For example, a suitable multipolar electrode may include a center cathode electrode that is flanked by two anodes, where the anodal electrodes are connected together, effectively sharing a charge. The electrodes may be circumferential in shape (e.g., annular) and have a diameter ranging from 0.25 mm to 10 mm, and a width from 0.25 mm to 10 mm. The inter-electrode spacing may have a range from 0.5 mm to 15 mm. Moreover, the electrodes may have varying impedances, to better contour the electric field that will block the nerve. For example, the anode and cathode may be present on only a portion of a radial surface of the electrode assembly. It is contemplated that the electrodes may be made by placing the anode and/or cathode on only a portion of the electrode surface and/or shielding or insulation may cover portions of the anode and cathode so the anode and cathode are present on only a portion of the radial surface of the electrode assembly.

According to another aspect of the system invention, the one or more electrodes may be one or more transcutaneous electrodes defining a generally uniform skin contacting surface for placement on the intact skin over a target nerve to selectively block nerve signal transmission in the nerve target underlying the one or more electrodes without eliciting a painful sensation; desirably at frequencies of greater than about 30 kilohertz and amplitudes less than about 25 milliamps. In an embodiment, the electrode may be selected to provide the optimal stimulation depth, selectivity and/or avoidance of painful sensations. For example, a conventional TENS electrode may be utilized. In other embodiments, such electrodes will define a generally uniform skin contacting surface. The skin contacting surface of each electrode is desirably an area of from about 1.5 mm$^2$ to about 100 mm$^2$. For example, the generally uniform skin contacting surface may have an area of from about 3.5 mm² to about 40 mm². The electronic control system may desirably provide electrical stimulation that further includes a carrier frequency ranging from about 5 kilohertz to about 1 megahertz such that the carrier frequency is greater than the frequency of the electrical stimulation used to block nerve signal transmission. Such a carrier frequency may also be used with the percutaneous electrode described above.

The present invention also encompasses a method for selectively blocking nerve fiber activity which includes the steps of identifying a target nerve and delivering electrical stimulation to the target nerve to block nerve signal transmission of A-fibers in the target nerve providing motor function and/or low-threshold sensory function such that the nerve signal transmission of the C-fibers in the target nerve is not blocked. In an aspect of the method, the step of delivering electrical stimulation to the target nerve may involve first delivering electrical stimulation to the target nerve at a frequency, amplitude, and/or waveform sufficient to block nerve signal transmission of both A-fibers and C-fibers in the target nerve and then changing the frequency, amplitude and/or waveform of the electrical stimulation so nerve signal transmission of the A-fibers in the target nerve providing motor function and/or low-threshold sensory function is blocked and so the nerve signal transmission of the C-fibers in the target nerve is not blocked. In another aspect of the method, the step of delivering electrical stimulation to the target nerve may involve first delivering electrical stimulation at an amplitude and/or frequency and/or waveform that does not block nerve signal transmission of both A-fibers and C-fibers in the target nerve and then changing the amplitude and/or the frequency and/or waveform of the electrical stimulation so nerve signal transmission of the A-fibers in the target nerve providing motor function and/or low-threshold sensory function is blocked and so the nerve signal transmission of the C-fibers in the target nerve is not blocked.

According to an aspect of the invention, method may involve the steps of identifying a target nerve; delivering an electrical stimulation at an initial frequency and amplitude to the target nerve; determining an electrical stimulation frequency and/or amplitude threshold sufficient to block nerve signal transmission in only one of A-fibers or C-fibers in the target nerve; and then delivering electrical stimulation to the target nerve at a frequency and amplitude to block nerve signal transmission of C-fibers in the target nerve such that the nerve signal transmission of the A-fibers in the target nerve providing motor function and/or low-threshold sensory function is not blocked.

According to the method, the step of delivering electrical stimulation to the target nerve may be carried out by positioning an electrode on, around or adjacent the target nerve and delivering electrical stimulation to the target nerve. The electrical stimulation may be delivered utilizing a nerve cuff having at least a blocking electrode to contact the target nerve and may further include a stimulating electrode(s) located on the cuff. Desirably, the blocking electrode is located on the cuff to contact the target nerve orthodromic to the stimulating electrode. The electrodes used for stimulation and/or blocking may be operated in a monopolar and/or multipolar fashion. Monopolar stimulation and/or blocking require a return electrode be placed at some distance from the cathode electrode. Preferably, stimulation and/or blocking will be delivered in a bipolar or multipolar fashion, where each electrode ensemble has an anode region for contacting the target nerve and a cathode region for contacting the target nerve. The nerve cuff may further include a recording electrode ensemble located on the cuff to contact the target nerve orthodromic to the blocking electrode, the recording electrode ensemble having an active electrode for contacting the target nerve, an indifferent electrode and a reference electrode. It is contemplated that the recording electrode ensemble may utilize as few as two electrodes or the recording electrode ensemble may utilize more electrodes to stabilize the recorded signal.

According to the method, the step of delivering electrical nerve blocking stimulation to the target nerve may be carried by positioning a percutaneous electrode in the vicinity of a target nerve by way of a paddle, cylindrical catheter or needle, wire form or the like; desirably at frequencies less than about 30 kilohertz and at amplitudes less than about 25 milliamps. For example, the frequencies may range from about 0 kilohertz (just above 0 kilohertz) to about 30 kilohertz and the amplitudes may range from about 0.5 milliamps to about 25 milliamps. Desirably, the one or more electrode ensembles for percutaneous blocking may be monopolar, bipolar or multipolar, and may include one, two, three or more electrodes that are placed in the vicinity of the nerve. Each electrode ensemble has a cathode region. Monopolar configurations have a return electrode placed some distance away, and may be a sticky electrode placed on the patient's skin. Bipolar and multipolar electrode configurations have at least one cathode and one anode in the vicinity of the nerve. The electrode shape and size, and inter-electrode spacing(s) are specific to contouring the electrical field surrounding the nerve, to enable selective high frequency blocking. For example, a suitable multipolar electrode may include a center cathode electrode that is flanked by two anodes, where the anodal electrodes are connected together, effectively sharing a charge. The electrodes may be circumferential in shape (e.g., annular) and have a diameter ranging from 0.25 mm to 3 mm, and a width from 0.25 mm to 3 mm. The inter-electrode spacing may have a range from 0.5 mm to 10 mm. Moreover, the electrodes may have varying impedances, to better contour the electric field that will block the nerve.

According to another aspect of the method invention, the step of delivering electrical stimulation to the target nerve may be carried out by positioning one or more electrodes on the intact skin over the target nerve, each electrode defining a generally uniform skin contacting surface having an area of from about 1.5 mm² to about 100 mm² and delivering the electrical stimulation to the target nerve through the intact skin at frequencies less than about 30 kilohertz and amplitudes less than about 25 milliamps to selectively block nerve signal transmission in the nerve target underlying the one or more electrodes without eliciting a painful sensation. For example, the generally uniform skin contacting surface may have an area of from about 3.5 mm² to about 80 mm². The method may further include utilizing a carrier frequency ranging from about 5 kilohertz to about 1 megahertz such that the carrier frequency is greater than the frequency of the electrical stimulation used to block nerve signal transmission. The carrier frequency may be used with the percutaneous electrodes described above.

An exemplary system for practicing the immediately above-described method includes one or more electrodes; and an electronic control system electrically attached to each electrode; the electronic control system delivers electrical stimulation to a target nerve to block nerve signal transmission of A-fibers in the target nerve providing motor function and/or low-threshold sensory function such that the nerve signal transmission of the C-fibers in the target nerve is not blocked. For example, the electronic control system may first provide electrical stimulation to the target nerve utilizing the one or more electrodes at a frequency less than about 30 kilohertz to block nerve signal transmission of both A-fibers and C-fibers in the target nerve, and then reduce the frequency of the electrical nerve-blocking stimulation so nerve signal transmission of the A-fibers in the target nerve providing motor function and/or low-threshold sensory function is blocked and so the nerve signal transmission of the C-fibers in the target nerve is not blocked. In another example, the electronic control system may first deliver electrical stimulation to the target nerve at an amplitude and/or the frequency and/or waveform that does not block nerve signal transmission of both A-fibers and C-fibers in the target nerve and then changes the amplitude and/or frequency and/or waveform of the electrical stimulation so nerve signal transmission of the C-fibers in the target nerve is blocked and so the nerve signal transmission of the A-fibers in the target nerve providing motor function and/or low-threshold sensory function is not blocked.

The electronic control system desirably provides electrical stimulation to the target nerve through the one or more electrodes at frequencies less than about 30 kilohertz and amplitudes of less than about 25 milliamps. For example, the frequencies may range from about 10 kilohertz to about 30 kilohertz and the amplitudes may range from about 0.2 milliamps to about 15 milliamps.

According to an aspect of the system invention, the electrodes may be an electrode assembly to deliver electrical energy to a target nerve and the electronic control system provides electrical stimulation to the target nerve through the electrode assembly at frequencies less than about 30 kilohertz and amplitudes less than about 10 milliamps.

The electrode assembly may be a nerve cuff having at least a blocking electrode to contact the target nerve and may further include a stimulating electrode(s) located on the cuff. Desirably, the blocking electrode is located on the cuff to contact the target nerve orthodromic to the stimulating electrode. The electrodes used for stimulation and/or blocking may be operated in a monopolar and/or multipolar fashion. Monopolar stimulation and/or blocking require a return electrode be placed at some distance from the cathode electrode. Preferably, stimulation and/or blocking will be delivered in a bipolar or multipolar fashion, where each electrode ensemble has an anode region for contacting the target nerve and a cathode region for contacting the target nerve. The nerve cuff may further include a recording electrode ensemble located on the cuff to contact the target nerve orthodromic to the blocking electrode, the recording electrode ensemble having an active electrode for contacting the target nerve, an indifferent electrode and a reference electrode. It is contemplated that the recording electrode ensemble may utilize as few as two electrodes or the recording electrode ensemble may utilize more electrodes to stabilize the recorded signal.

According to another aspect of the system invention, the electrodes may be an electrode assembly to deliver electrical nerve blocking stimulation to the target nerve by positioning a percutaneous electrode in the vicinity of a target nerve by way of a paddle, cylindrical catheter or needle, wire form or the like: desirably at frequencies less than about 30 kilohertz and at amplitudes less than about 50 milliamps. For example, the frequencies may range from about 0 kilohertz to about 30 kilohertz and the amplitudes may range from about 0.5 milliamps to about 25 milliamps. Desirably, the one or more electrode ensembles for percutaneous blocking may be monopolar, bipolar or multipolar, and may include one, two, three or more electrodes that are placed in the vicinity of the nerve. Each electrode ensemble has a cathode region. Monopolar configurations have a return electrode placed some distance away, and may be a sticky electrode placed on the patient's skin. Bipolar and multipolar electrode configurations have at least one cathode and one anode in the vicinity of the nerve. The electrode shape and size, and inter-electrode spacing(s) are specific to contouring the electrical field surrounding the nerve, to enable selective high frequency blocking. For example, a suitable multipolar electrode may include a center cathode electrode that is flanked by two anodes, where the anodal electrodes are connected together, effectively sharing a charge. The electrodes may be circumferential in shape (e.g., annular) and have a diameter ranging from 0.25 mm to 10 mm, and a width from 0.25 mm to 10 mm. The inter-electrode spacing may have a range from 0.5 mm to 10 mm. Moreover, the electrodes may have varying impedances, to better contour the electric field that will block the nerve.

According to another aspect of the system invention, the one or more electrodes may be transcutaneous electrodes defining a generally uniform skin contacting surface for placement on the intact skin over a target nerve to selectively block nerve signal transmission in the nerve target underlying the one or more electrodes without eliciting a painful sensation. In an embodiment, the electrode may be selected to provide the optimal stimulation depth, selectivity and/or avoidance of painful sensations. For example, a conventional TENS electrode may be utilized. In other embodiments, such electrodes will define a generally uniform skin contacting surface. The skin contacting surface of each electrode is desirably an area of from about 1.5 $mm^2$ to about 100 $mm^2$. For example, the generally uniform skin contacting surface may have an area of from about 3.5 $mm^2$ to about 40 $mm^2$. When such electrodes are used to deliver electrical energy through the skin, the frequencies of the electrical stimulation are less than about 30 kilohertz and the amplitudes are desirably less than about 50 milliamps. The electrical nerve-blocking stimulation may further include a carrier frequency ranging from about 5 kilohertz to about 1 megahertz such that the carrier frequency is greater than the frequency of the electrical stimulation use to block nerve signal transmission. The carrier frequency may be used with the percutaneous electrodes described above.

The present invention also encompasses an electrode assembly for delivering electrical energy to a target nerve. The electrode assembly includes a nerve cuff or collar having a stimulating electrode and a blocking electrode located on the cuff to contact the target nerve orthodromic to the stimulating electrode. Each electrode has at least one cathode region for contacting the target nerve and, optionally, may have one or more anode regions for contacting the target nerve. The electrode assembly may further include a recording electrode located on the cuff to contact the target nerve orthodromic to the blocking electrode. The recording electrode has an active electrode for contacting the target nerve and a reference electrode.

The present invention also encompasses a medical procedure kit for performing a procedure for selectively blocking nerve fiber activity utilizing a nerve cuff or collar. The kit includes a container. The container further includes one or more electrode assemblies, each electrode assembly including a nerve cuff or collar having a stimulating electrode and a blocking electrode located on the cuff to contact a target nerve orthodromic to the stimulating electrode, each electrode having at least one cathode region for contacting a target nerve and, optionally, one or more anode regions for contacting the target nerve. The container also includes electrical leads for connecting the one or more electrode assemblies to an electronic control system for delivering electrical stimulation to a target nerve utilizing the one or more electrode assemblies to selectively block nerve fiber activity. The medical procedure kit may also include one or more recording electrodes located on the cuff to contact the target nerve orthodromic to the blocking electrode. The recording electrode has an active electrode for contacting the target nerve and a reference electrode. The kit may include any manner or number of additional items for enabling the procedure For example, the kit may include one or more containers of antiseptic, antiseptic wipes, skin-prep liquids or wipes, electrically conductive liquids or gels. Similarly, the kit may include any combination of drape, site dressings, tape and so forth.

The present invention also encompasses a medical procedure kit for performing a procedure for selectively blocking nerve fiber activity utilizing a percutaneous electrode. The kit includes a container. The container further includes one or more electrode assemblies, each electrode assembly including a paddle, cylindrical catheter or needle, wire form or the like to deliver electrical energy percutaneously to a target nerve. Desirably, the one or more electrode ensembles for percutaneous blocking may be monopolar, bipolar or multipolar, and may include one, two, three or more electrodes that are placed in the vicinity of the nerve. Each electrode ensemble has a cathode region. Monopolar configurations include a sticky electrode to be placed on the patient's skin. Bipolar and multipolar electrode configurations have at least one cathode and one anode. The container also includes electrical leads for connecting the one or more electrode assemblies to an electronic control system for delivering electrical stimulation to a target nerve utilizing the one or more electrode assemblies to selectively block nerve fiber activity. The kit may include any manner or number of additional items for enabling the procedure. For example, the kit may include one or more containers of antiseptic, antiseptic wipes, skin-prep liquids or wipes, electrically conductive liquids or gels. Similarly, the kit may include any combination of drape, site dressings, tape and so forth.

The present invention also encompasses a medical procedure kit for performing a procedure for selectively blocking nerve fiber activity by delivering electrical energy through intact skin. The kit includes a container. The container further includes one or more electrodes, each electrode defines a generally uniform skin contacting surface, and the skin contacting surface of each electrode has an area of from about 1.5 mm$^2$ to about 40 mm$^2$. The kit also includes electrical leads for connecting the one or more electrodes to an electronic control system for delivering electrical stimulation utilizing the one or more electrodes through the intact skin to selectively block nerve fiber activity in a target nerve underlying the one or more electrodes without eliciting pain sensations. The medical procedure kit may also include one or more anodes, each anode having a skin contacting surface. The skin contacting surface of each anode desirably has at least the same surface area (or greater) as the skin contacting surface of the electrode. The kit may include any manner or number of additional items for enabling the procedure. For example, the kit may include one or more containers of antiseptic, antiseptic wipes, skin-prep liquids or wipes, electrically conductive liquids or gels. Similarly, the kit may include any combination of drape, site dressings, tape, and so forth.

These and other features and advantages of the invention will become more apparent to one skilled in the art from the following description and claims when read in light of the accompanying drawings.

BRIEF DESCRIPTION OF THE DRAWINGS

FIG. 2 is a perspective side view of an exemplary electrode assembly utilized for delivering electrical energy directly to the vicinity of a target nerve to selectively block nerve fiber activity.

FIG. 3 is perspective side view of another exemplary electrode assembly utilized for delivering electrical energy directly to the vicinity of a target nerve to selectively block nerve fiber activity.

FIG. 4 is a perspective side view showing a detail of an exemplary electrode as illustrated in FIG. 3.

DEFINITIONS

Figure 1:
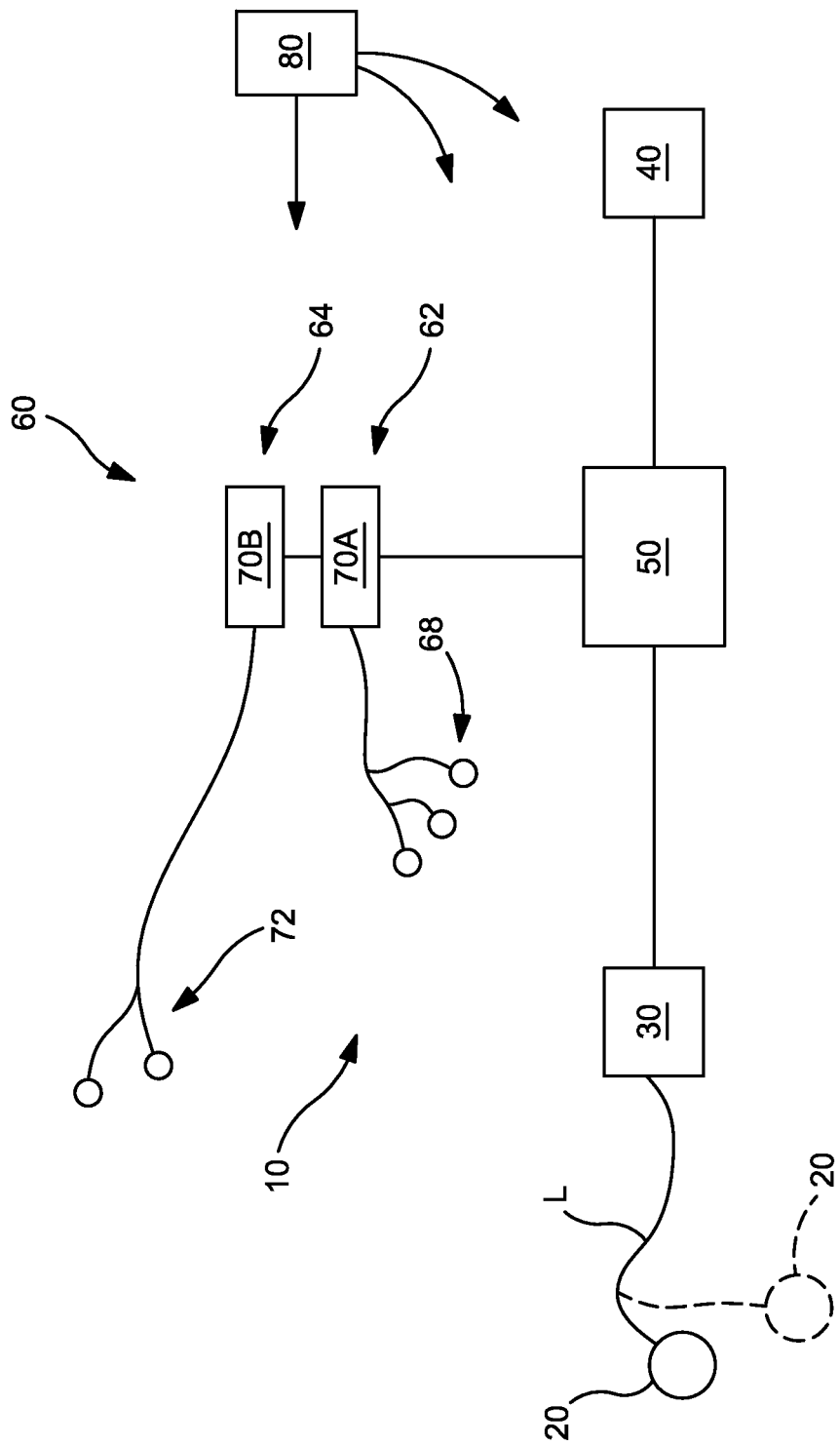
FIG. 1 is schematic diagram of an exemplary system for selectively blocking nerve fiber activity.

As used herein, the terms "A-fiber" or "A-fibers" refer to myelinated afferent or efferent peripheral axons of the somatic nervous system with conduction velocities between about 2 meter per second (m/s) to more than 100 m/s. A-fibers have a diameter of about 1 to 22 micrometers (μm) and include the alpha, beta, delta, and gamma fibers. Each A-fiber has dedicated Schwann cells forming the myelin sheath around it. The myelin sheath has a high content of lipids that increases the membrane resistance and contributes to the high conduction velocity of action potentials which are carried from one to the next intersection between two myelin covered segments. Generally speaking, A-fibers are associated with proprioception, somatic motor function, sensations of touch and pressure and also some limited sensations of pain and temperature.

As used herein, the terms "carrier frequency", "carrier signal" or "carrier wave" refer to a waveform that has a fixed center frequency that has been modulated (i.e., altered) in a way that its amplitude, frequency, phase or some other property varies. The frequency is measured in Hertz (cycles per second). For purposes of the present invention, a carrier frequency is selected to reduce the skin's impedance, helping the modulating frequency to activate neural structures beneath the skin. Desirably, a carrier frequency is a high frequency waveform.

As used herein, the term "C-fiber" or "C-fibers" refer to non-myelinated peripheral axons of the somatic nervous system with conduction velocities of less than about 2 m/s. C-fibers have a diameter of about 0.3 to 1.4 micrometers (μm) and include the dorsal root and sympathetic fibers and are primarily associated with sensations like pain and temperature and some limited mechanoreception and reflex responses.

As used herein, the term "disposable" refers to a product that is so inexpensive that it may economically be discarded after only a single use. Products that are "disposable" are typically intended for single use. The term "single-use" refers to a product that is intended to be used for only once and is not intended to be re-used, re-conditioned, restored or repaired after that use. These products offer advantages in clinical settings by reducing the potential for contamination or infection. In addition, these products can enhance work flow since they are not collected and assembled for reprocessing and reuse.

As used herein, the terms "electrical stimulation sufficient to block nerve signal transmission" or "electrical nerve-blocking stimulation" or "electrical nerve-block" refer to electrical energy in a waveform that, upon reaching an axon of a neuron, blocks the propagation of action potentials through the stimulation site.

As used herein, the term "intact skin" refers to skin that is sound, unbroken and uninjured, or not altered in any meaningful way such as, for example, by fresh surgical incision, fresh piercing by an instrument such as a needle, trocar or the like.

As used herein, the terms "modulating frequency", "modulating signal" or "modulating wave" refer to a low to moderate frequency waveform that is used to block neural transduction. For purposes of the present invention, a modulating frequency is selected to provide electrical nerve blocking stimulation to block nerve signal transmission in an effective and safe manner.

As used herein, the term "nerve block" refers to an interrupting, hindering or preventing the passage of impulses along a neuron's axon within a nerve. The term also encompasses a form of regional anesthesia in which insensibility is produced in a part of the body by interrupting, hindering or preventing the passage of impulses along a neuron's axon, making the nerve inoperable.

As used herein, the terms "nerve cuff", "nerve collar" and/or "nerve hook" refer to electrode assemblies providing electrical interfaces with nerve fibers for applying or electrical energy or monitoring neural activity. Exemplary nerve cuffs are described at, for example, Journal of Neuroscience Methods 64 (1996) 95-103 "Cuff Electrodes For Chronic Stimulation and Recording of Peripheral Nerve Activity"; Loeb, G. E., Peck, R. A. Nerve cuffs may be spiral wound and have one or more electrodes arrayed radially or axially and may be shielded to isolate the electrodes from background electrical signals. Other exemplary nerve cuff devices are described at, for example, U.S. Pat. No. 5,344,438 issued Sep. 6, 1994 to Testerman et al. for "Cuff Electrode".

As used herein, the terms "percutaneous" and/or "percutaneously" refer to electrical stimulation applied utilizing one or more electrodes penetrating through the surface of the skin so an electrode delivering electrical stimulation to a target nerve beneath the skin is also located beneath the skin. It is contemplated that return electrodes or anodes may be located beneath the skin or on the surface of the skin.

As used herein, the term "percutaneous electrode" refers to electrode assemblies inserted through the skin and directed into the vicinity of the nerve (mm to cm distance) in a minimally invasive fashion to electrically affect neural physiology.

As used herein, the terms "pain sensation" or "painful sensation" refer to a highly disagreeable sensation generated by the activation of sensory nociceptors. Nociception describes the perception of acute pain.

As used herein, the term "target nerve" refers to mixed nerves containing motor nerve fibers and sensory nerve fibers. It may additionally refer to sensory nerves containing only sensory nerve fibers and/or to motor nerves containing only motor nerve fibers.

As used herein, the terms "transcutaneous" and/or "transcutaneously" refer to electrical stimulation applied non-invasively utilizing one or more electrodes applied to the surface of the skin so the electrical stimulation passes through the skin.

DETAILED DESCRIPTION OF THE INVENTION

In describing the various embodiments of the present invention, as illustrated in the figures and/or described herein, specific terminology is employed for the sake of clarity. The invention, however, is not intended to be limited to the specific terminology so selected, and it is to be understood that each specific element includes all technical equivalents that operate in a similar manner to accomplish similar functions.

Referring now to FIG. 1 of the drawings, there is illustrated a system for delivering electrical stimulation to selectively block nerve fiber activity in a target nerve. Generally speaking, the electrical stimulation may be delivered to the target nerve utilizing an electrode that may be in the form of an electrode assembly that can include a nerve cuff or collar to selectively block nerve fiber activity in a target nerve. Alternatively and/or additionally, the electrical stimulation may be delivered through intact skin to block nerve signal transmission in an underlying target nerve (i.e., delivered in a transcutaneous or transdermal manner) without use of an instrument or electrode that physically penetrates the skin by incision, piercing, or the like to be physically adjacent the target nerve. In other words, electrical stimulation is delivered directly to intact skin to block nerve signal transmission in an underlying target nerve in a non-invasive manner. The intact skin may be intact mammalian skin.

The system includes multiple devices to control and deliver predetermined electrical pulses at predetermined frequencies and amplitudes to one or more target nerve(s). In general, the system, referenced as the schematic system 10 in FIG. 1, may include one or more electrode 20 (shown diagrammatically in FIG. 1 and not in any specific detail) that is connected by an electrical lead "L" to the rest of the system 10—which includes a pulse generator 30, a user interface 40, and a controller 50. The system may also include a patient monitor system 60 and an isolated power system 80. While an experimental-scale system is shown and described, it is contemplated that a more compact unit could be used to control and deliver the desired electrical stimulation.

Referring generally to FIGS. 2 through 4 of the drawings, and more specifically to FIG. 2, there is illustrated in side perspective view an exemplary electrode 20 for delivering electrical energy directly to a target nerve, the electrode 20 is in the form of an electrode assembly 302 that includes a nerve cuff or collar 304 having a stimulating electrode 306 and a blocking electrode 308 located on the cuff to contact the target nerve orthodromic to the stimulating electrode 306. Each electrode has an anode region 310 for contacting the target nerve "N" and a cathode region 312 for contacting the target nerve "N". The arrow "A" represents the orthodromic direction for this exemplary nerve "N".

Referring more specifically to FIG. 3 of the drawings, there is illustrated in side perspective view another exemplary a stimulating electrode 20 that further includes a recording electrode 314 located on the cuff 304 to contact the target nerve orthodromic to the blocking electrode 308. The recording electrode 314 also has an active electrode 316 for contacting the target nerve and a reference electrode (not shown). FIG. 4 is a side perspective view illustration of an exemplary electrode assembly 302 that includes the nerve cuff or collar 304 of FIG. 2 positioned in contact with an exemplary target nerve "N". As can be seen in FIG. 4, the simulating electrode 306 and the blocking electrode 308 are in contact with the target nerve "N".

Figure 14A:
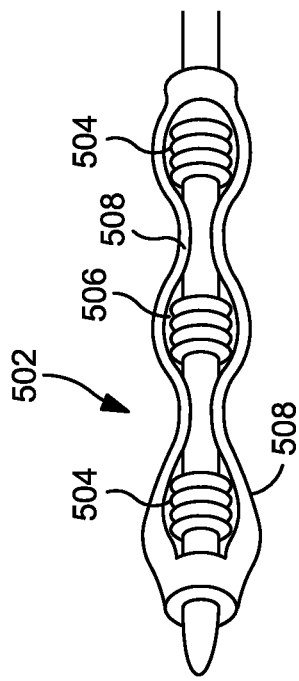
FIGS. 14A and 14B are side perspective views of exemplary percutaneous electrodes for delivering electrical energy directly to the vicinity of a target nerve to selectively block nerve fiber activity in which an anode and cathode are present on only a portion of the radial surface of the electrode.
Figure 14B:
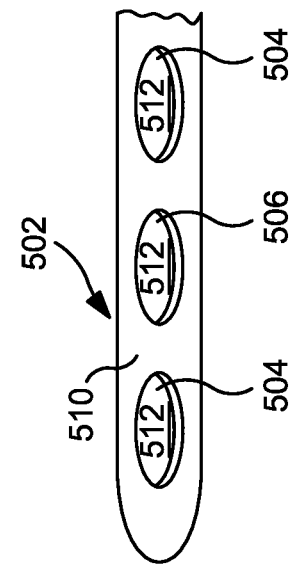
Figure 13:
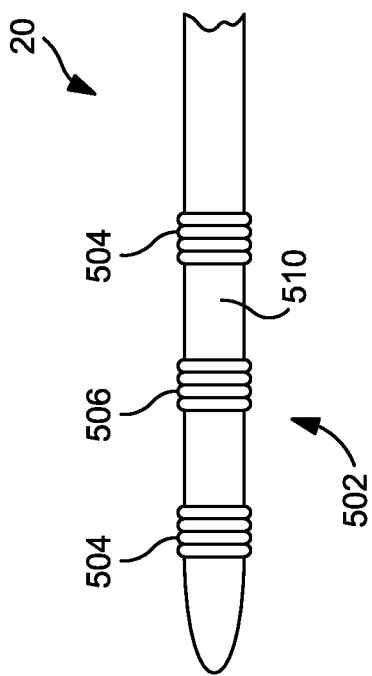
FIG. 13 is a side perspective view of an exemplary percutaneous electrode assembly utilized for delivering electrical energy directly to the vicinity of a target nerve to selectively block nerve fiber activity.
Figure 15:
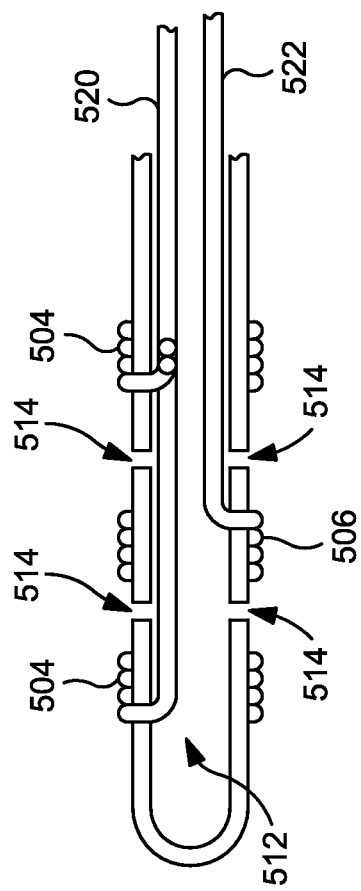
FIG. 15 is a side cross-sectional view of an exemplary percutaneous electrode assembly including a lumen or passageway for delivering fluid therethrough, the electrode assembly utilized for delivering electrical energy directly to the vicinity of a target nerve to selectively block nerve fiber activity.

Referring generally to FIGS. 13 through 15 of the drawings, and more specifically to FIG. 13, there is illustrated in side perspective view an exemplary electrode 20 for delivering electrical energy directly to a target nerve, the electrode 20 is in the form of a percutaneous blocking electrode(s) 502 that is placed nearby a target nerve. Each blocking electrode 502 used in a bipolar or multi-polar fashion has an anode 504 and a cathode 506 placed nearby a target nerve "N". Monopolar percutaneous blocking electrodes have a cathode 506 located nearby a nerve, and a return electrode (i.e., anode) positioned some distance away (e.g., in the form of a patch electrode on the surface of the skin). Bipolar and multipolar electrode configurations have at least one cathode and one anode in the vicinity of the nerve. The electrode shape and size, and inter-electrode spacing are specific to contouring the electrical field surrounding the nerve, to enable selective high frequency blocking. For example, a suitable multipolar electrode may include a center cathode electrode 506 that is flanked by two anodes 504, where the anodal electrodes are connected together, effectively sharing a charge. The electrodes may be circumferential in shape (e.g., disposed radially at the surface of the electrode) and have a diameter ranging from 0.25 mm to 10 mm, and a width from 0.25 mm to 10 mm. For example, the electrodes may have a diameter ranging from about 0.25 mm to 5 mm, and a width from 0.25 mm to 5 mm. As another example, the electrodes may have a diameter ranging from about 0.25 mm to 3 mm, and a width from 0.25 mm to 3 mm. The inter-electrode spacing may have a range from 0.5 mm to 10 mm. Moreover, the electrodes may have varying impedances, to better contour the electric field that will block the nerve.

Referring now to FIG. 14A, there is illustrated a side perspective view of an exemplary percutaneous electrode 502 for delivering electrical energy directly to the vicinity of a target nerve to selectively block nerve fiber activity and in which an anode 504 and cathode 506 are present on only a portion of the radial surface of the electrode assembly. As can be seen in FIG. 14A, shielding 508 covers portions of the anode 504 and cathode 506 so the anode and cathode are present on only a portion of the radial surface of the electrode assembly. FIG. 14B illustrates anodes 504 and a cathode 506 in the form of small plates or tabs 512 located on the radial surface 510 of the percutaneous electrode 502. While FIG. 14A illustrates an exemplary percutaneous electrode in multipolar configuration, the electrode may have a bipolar or monopolar configuration.

FIG. 15 is a side cross-sectional view of an exemplary percutaneous electrode 502 including a lumen or passageway 512 for delivering fluid therethrough. The percutaneous electrode 502 may define a lumen or passageway 512 through the electrode to channel a fluid through the electrode and may further define openings 514 in communication with the lumen or passageway 512 to deliver fluid out through the electrode. Desirably, the electrode assembly defines openings 514 adjacent the anode 504 and cathode 506. However, these openings 514 may be at other locations. The lumen or pathway 512 may be integrated with or connected to a tube to deliver fluid to the lumen. The delivery tube can have a standard Luer connection or similar connection.

As can be seen in this illustration, the anodes 504 are paired or joined by a lead 520 and the cathode 506 is connected to a different lead 522. The electrode assembly may be connected to a fluid flow path in communication with a fluid pump; the fluid flow path may be configured to deliver a fluid to be dispensed to a patient through the electrode assembly. Alternatively and/or additionally, the electrode assembly may be connected to a bolus reservoir in communication with a bolus flow path. The bolus reservoir may be configured to selectively permit fluid to be dispensed to a patient through the electrode assembly. The arrangement may include a patient operable actuator configured to dispense fluid from the bolus reservoir. In such configuration, the percutaneous electrode can be used to deliver medicinal fluid such as liquid anesthetic in addition to nerve blocking electrical stimulation. The medicinal liquid may be a bolus of anesthetic or it may be an antibiotic material, antimicrobial material or an electrolytic solution to enhance delivery of electrical stimulation. Exemplary fluid pumps, fluid flow paths and bolus delivery configurations or systems are described in U.S. Pat. No. 6,981,967 issued Jan. 3, 2006 to Massengale et al., for "Large Volume Bolus Device and Method", incorporated herein by reference.

Figure 5:
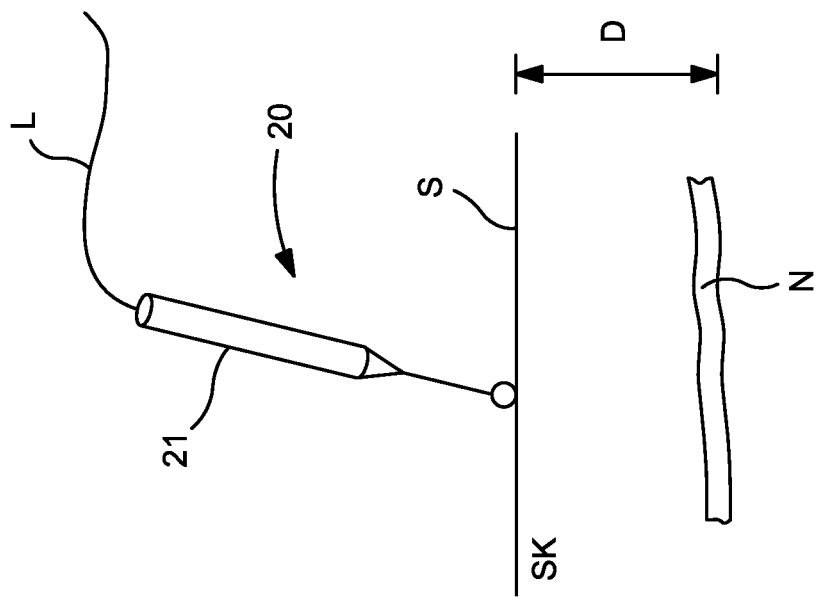
FIG. 5 is a perspective side view of an exemplary system for delivering electrical energy through the intact skin to a target nerve in order to selectively block nerve fiber activity.

According to another aspect of the system invention, the one or more electrodes 20 may be a transcutaneous electrode 21. As can be seen in FIG. 5 of the drawings, there is illustrated a transcutaneous electrode 21 placed in contact with the surface "S" of the skin "SK" above a target nerve "N". The separation between the surface "S" of the skin and the target nerve "N" is identified as distance "D". The distance "D" is on the order of millimeters, where larger distances require more intensive stimulation to achieve a nerve block. Mild amounts of pressure may be applied to the transcutaneous electrode to decrease the electrode-skin distance, reducing the effective stimulation intensity and improve subject comfort.

Transcutaneous Electrode.

Figure 6:
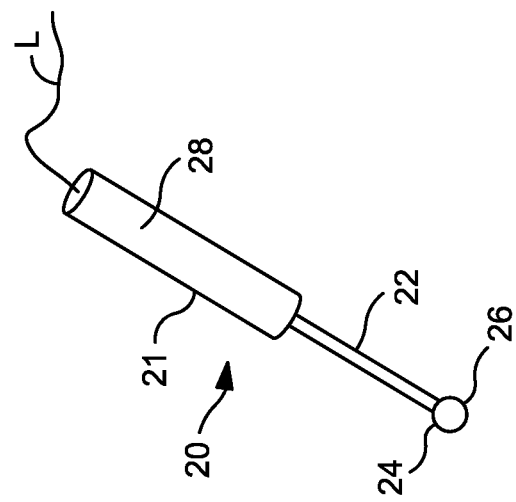
FIG. 6 is a perspective side view of an exemplary electrode utilized in a system for delivering electrical energy through the intact skin to a target nerve in order to selectively block nerve fiber activity (a transcutaneous nerve block system).

Referring to FIG. 6, the overall shape of the one or more exemplary transcutaneous electrodes 21 is such that it allows an operator to precisely place the electrode tip in the proximity of a targeted nerve. In one aspect of the disclosure, the electrodes may include an elongated shaft 22 having a tip 24 defining a generally uniform skin contacting surface 26 one end, and a support such as a handle 28 at the opposite end. An electrical lead "L" may be integrated with the electrode 20 or may be attached using a conventional electrical connector. The skin contacting surface 26 of the tip 24 is an electrically conductive surface.

The transcutaneous electrode 21 is constructed from a metal that is conductive and biocompatible, such as stainless steel. The handle 28, if used, may be large enough for a clinician to comfortably grip, and may be made of material that will minimize the risk of accidental shock, e.g., non-conductive plastic. The transcutaneous electrode 21 is electrically connected to a pulse generator 30 by way of an electrical lead or lead-wire.

The tip 24 desirably has a blunt end, desirably spherical, spheroidal, hemi-spherical or hemi-spheroidal in shape. The shaft diameter, for a distance of at least about one inch from the tip, is less than or equal to the tip diameter. One possible electrode that meets such criteria is the pedicle screw probe electrode, model PSP-1000, available from Axon Systems, Inc. However, other electrode configurations are contemplated.

Generally speaking, the transcutaneous electrodes 21 may desirably define a generally uniform skin contacting surface 26. Desirably, the skin contacting surface of each transcutaneous electrode has an area of from about 1.5 mm$^2$ to about 100 mm$^2$. Desirably, the skin contacting surface has an area of from about 3.5 mm$^2$ to about 20 mm$^2$. The tip of the electrode may have an oval, elliptical or circular cross-section. Desirably, the tip 24 of the transcutaneous electrode 21 is circular and may be less than 7 mm in diameter; or less than 5 mm in diameter, or most desirably is about 2.5 mm diameter. A smaller electrode is less likely to activate the skin's pain receptors and is more controllable so it is easier to position the electrode an adequate distance from superficial muscle groups and non-target nerves.

In one aspect of the invention, the shaft 22 may be coated with TEFLON® fluoropolymer or other conventional insulating material to create a higher field density at the tip. The relatively small tip 24 corresponds to a relatively large current density of about 942 mA/cm$^2$ (20 mA peak current; 1.5 mm$^2$ surface area), to 1 mA/cm$^2$ and most desirably, 140 mA/cm$^2$ (calculated with a 2.5 mm tip diameter; square-wave pulses; 50% duty cycle).

Figure 7:
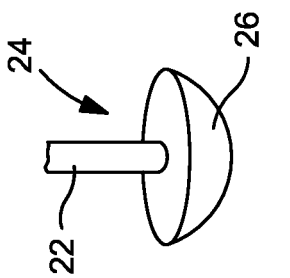
FIG. 7 is a perspective side view showing a detail of an exemplary electrode as illustrated in FIG. 6.
Figure 8:
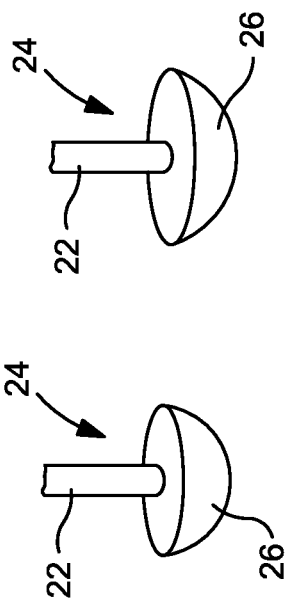
FIG. 8 is a perspective side view showing a detail of another exemplary electrode utilized in transcutaneous nerve block system.
Figure 9:
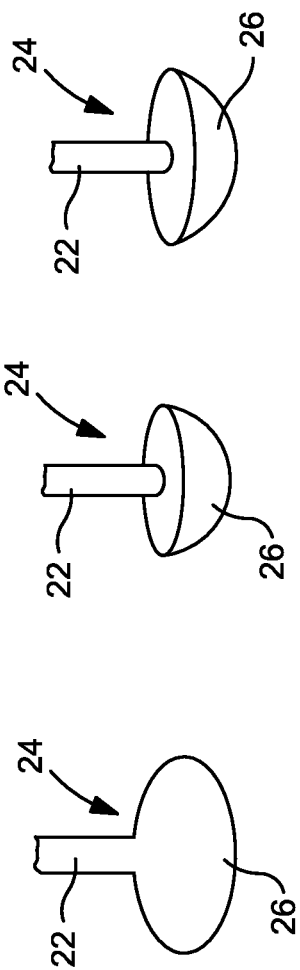
FIG. 9 is a perspective side view showing a detail of another exemplary electrode utilized in transcutaneous nerve block system.
Figure 10:
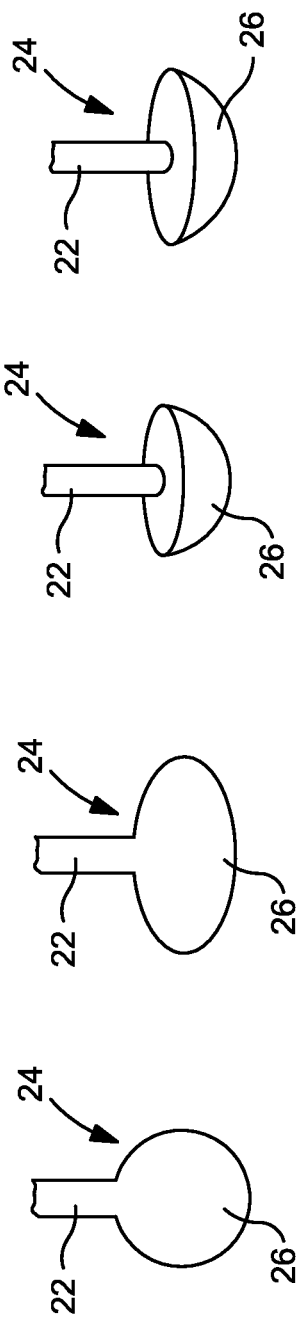
FIG. 10 is a perspective side view showing a detail of another exemplary electrode utilized in transcutaneous nerve block system.

FIG. 7 is an illustration of an exemplary electrode tip 24 extending from the shaft 22 of the electrode. The electrode tip 24 has a generally spherical shape to provide a generally uniform skin contacting surface 26. FIG. 8 is an illustration of another exemplary electrode tip 24 extending from the shaft 22 of the electrode. The electrode tip 24 has a generally spheroidal shape (e.g., an oblate spheroid) to provide a generally uniform skin contacting surface 26. FIG. 9 is an illustration of yet another exemplary electrode tip 24 extending from the shaft 22 of the electrode. The electrode tip 24 has a generally hemi-spherical shape to provide a generally uniform skin contacting surface 26. FIG. 10 is an illustration of still yet another exemplary electrode tip 24 extending from the shaft 22 of the electrode. The electrode tip 24 has a generally hemi-spheroidal shape (e.g., about one-half of an oblate spheroid) to provide a generally uniform skin contacting surface 26. Of course, it is contemplated that a variety of other shapes and configurations may be utilized.

Figure 11:
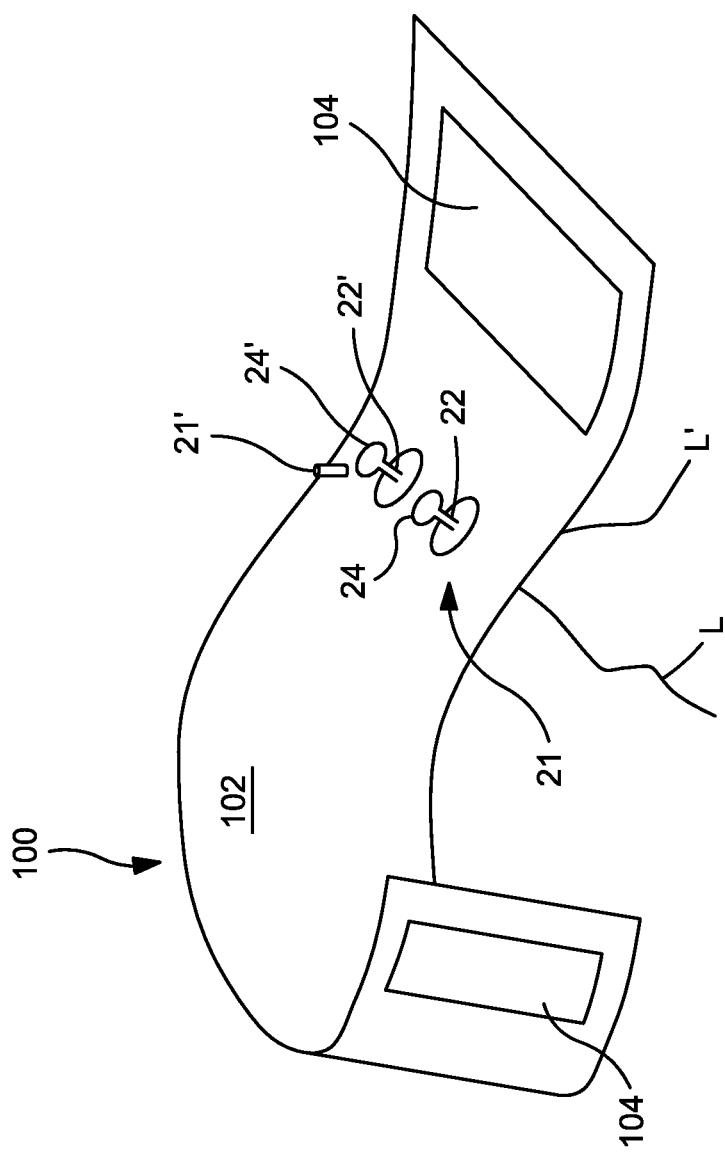
FIG. 11 is a perspective side view of an exemplary holding device which may be utilized with one or more electrodes and/or anodes for delivering electrical energy through the intact skin to a target nerve in order to selectively block nerve fiber activity.

In one aspect, it is contemplated that the electrode shaft 22 may be truncated to the tip 24 or near the tip (leaving only a small portion of shaft 22) and attached or otherwise connected to a holding device 100 that can securely position the transcutaneous electrode 21 over the targeted nerve during the stimulation procedure. For example, FIG. 11 shows one example of a holding device 100 to which a transcutaneous electrode 21 is placed. The transcutaneous electrode 21 has a shaft 22 and a tip 24 and may be connected to a pulse generator 30 through an electrical lead "L". An optional second transcutaneous electrode 21' may also be incorporated with the holding device 100. The optional second electrode 21' may be an additional electrode or it may be an anode. The optional second electrode 21' has a shaft 22' and a tip 24' and may be connected to a pulse generator 30 through an electrical lead "L'". It is contemplated that additional electrodes in the form of transcutaneous electrodes and/or anodes may be utilized. The holding device may have a strap 102 such as illustrated in FIG. 11. The strap 102 may have fastening components 104 such as, for example, cohesive materials or mechanical fasteners (e.g., hook and loop systems, clips, snaps, pins, etc.).

The electrode ensemble may deliver stimulation in monopolar fashion or mode. In this monopolar mode, one or more stimulating electrode(s) is positioned over the target nerve and a second dispersive electrode with a relatively larger surface area is positioned on a surface of the patient's body to complete the circuit. Alternatively, the stimulation may be delivered in a bipolar fashion or mode and the above-described system may further include one or more anodes, each anode having a skin contacting surface. When the stimulation is delivered in a bipolar fashion or mode, the one or more electrode(s) (also referred to as a "cathode(s)") is positioned over the target nerve and one or more anode(s) is positioned on the skin over the target nerve to preferentially concentrate the delivery of electrical energy between the cathode(s) and anode(s). In either mode, the electrodes should be positioned a sufficient distance away from each other, to avoid shunting and a possible short-circuit. The skin contacting surface of each anode will desirably have at least the same or greater surface area as the skin contacting surface of the stimulating electrode(s).

Stimulator.

The electrodes 20 or 21 (e.g., nerve cuff or transcutaneous electrode) may be connected to a pulse generator 30 through an electrical lead "L". Desirably, the pulse generator 30 is a bipolar constant current stimulator. One exemplary stimulator is the DIGITIMER DS5 peripheral electrical stimulator available from Digitimer Ltd., England. Other constant current and constant voltage pulse generators may be used. Exemplary generators may include Model S88x, S48, or SD9 Stimulators available from Grass Technologies, a subsidiary of Astro-Med, Inc., West Warwick, R.I., USA.

Monopolar stimulation may also be used to block neural transduction, although the stimulation may be less effective.

User Interface.

The system may utilize a user interface 40. This user interface 40 may be in the form of a computer that interacts with the controller 50 and is powered by an isolation system 80, each described herein.

The computer operates software designed to record signals passed from the controller, and to drive the controller's output. Possible software includes Cambridge Electronic Design's (UK) SPIKE program. The software is programmable and can record and analyze electrophysiological signals, as well as direct the controller to deliver stimulation.

Patient Monitor System.

An optional patient monitor system 60 may be used. The patient monitoring system acquires, amplifies and filters physiological signals, and outputs them to the controller. The optional monitoring system includes a heart-rate monitor 62 to collect electrocardiogram signals, and muscle activity monitor 64 to collect electromyography signals. The heart-rate monitor 62 includes ECG electrodes 68 coupled with an alternating current (AC) amplifier 70A. The muscle activity monitor 64 includes EMG electrodes 72 coupled with an AC amplifier 70B. Other types of transducers may also be used. As described, all physiological signals obtained with the patient monitoring system are passed through an AC signal amplifier/conditioner (70A, 70B). One possible amplifier/conditioner is Model LP511 AC amplifier available from Grass Technologies, a subsidiary of Astro-Med, Inc., West Warwick, R.I., USA.

Isolated Power System.

All instruments are powered by an isolated power supply or system 80 to protect them from ground faults and power spikes carried by the electrical main. An exemplary isolated power system is available is the Model IPS115 Isolated Medical-grade Power System from Grass Technologies, a subsidiary of Astro-Med, Inc., West Warwick, R.I., USA.

Controller.

A controller 50 records waveform data and digital information from the patient monitor system 60, and can generate waveform and digital outputs simultaneously for real-time control of the pulse generator 30. The controller 50 may have onboard memory to facilitate high speed data capture, independent waveform sample rates and on-line analysis. An exemplary controller 50 may be a POWER 1401 data-acquisition interface unit available from Cambridge Electronic Design (UK).

Electrical Stimulation Parameters

Low and Moderate-Frequency Stimulation
1. Stimulation type: Constant-current, or constant-voltage stimulation
2. Delivery fashion: may be monophasic or biphasic (most desirable for blocking)
3. Waveform: square-wave; sinusoidal; pulse train
4. Pulse frequency: in order to selectively block A-fibers with the least amount of stimulation intensity, the pulse frequency may be about 0.1 Hz (i.e., above 0 hertz) to about 30 kHz, desirably 3 kHz to about 30 kHz, and more desirably 5 kHz to about 30 kHz. In order to block C-fibers with the least amount of stimulation intensity, the pulse frequency may be about 30 kHz (i.e., above 30 kilohertz) to about 100 kHz, desirably 30 kHz to about 75 kHz, and more desirably 40 kHz to 60 KHz.
5. Pulse duration: may be less than about 1000 µs; or less than about 5 µs; or most desirably 10 ρs for conduction blocking
6. Phase duration: (for biphasic pulses only) may be less than about 500 µs; or less than about 2.5 µs; or most desirably 5 µs for conduction blocking
7. Current: may be about 0.1 mA (i.e., above 0 mA) to about 25 mA. Generally speaking, when electrical stimulation is applied directly in the vicinity of the target nerve (i.e., using an electrode assembly that includes a nerve cuff, collar or a probe), the current should be less than about 10 mA. When the current is applied percutaneously or transcutaneously (i.e., through the intact skin), the current should be less than about 25 mA.
8. Current density (for Transcutaneous Electrode only): less than 942 mA/cm$^2$. The current density of the ideal stimulation for blocking with a hemispherical, 2.5 mm diameter electrode tip may be about 280 mA/cm$^2$, and most desirably, about 140 mA/cm$^2$.
9. Pulse period: (the amount of time between the start of one pulse to the start of the next pulse; it includes phase duration, intrapulse intervals, and interpulse intervals) may be less than about 1 millisecond (ms); or 0 ms, or most desirably about 0.02 ms for conduction blocking.
10. Pulse train: (burst of multiple pulses) may be delivered on the order of seconds to minutes. Each pulse train is separated by an off-time which is the interburst interval (variable, patient specific).

High-Frequency Stimulation
1. Stimulation type: Constant-current, or constant-voltage stimulation
2. Delivery fashion: may be monophasic or biphasic (most desirable)
3. Waveform: square-wave; sinusoidal; pulse train
4. Pulse frequency: may be about 30 kHz to 1 MHz; desirably 45 kHz to 1 MHz
5. Pulse duration: may be less than about 5 µs; or less than 0.5 µs; or most desirably 2.5 µs
6. Phase duration: (for biphasic pulses only) may be less than about 2.5 µs; or less than 0.25 µs; or most desirably 1.25 µs for each portion of the pulse.
7. Current: may be about 0.1 mA (i.e., above 0 mA) to 25 mA. Generally speaking, when electrical stimulation is applied directly in the vicinity of the target nerve (i.e., using an electrode assembly that includes a nerve cuff, collar or a probe), the current should be less than about 10 mA. When the current is applied transcutaneously (i.e., through the intact skin), the current should be less than about 25 mA.
8. Current density (for Transcutaneous Electrode only): (amount of current (mA) per unit area (cm$^2$) for a hemispherical, 2.5 mm diameter, electrode tip) may be less than about 70 mA/cm$^2$, and most desirably about 10 mA/cm$^2$.
9. Pulse train: (burst of multiple pulses) may be delivered on the order of milliseconds to seconds. Each pulse train is separated by an off time which is the interburst interval (variable, patient specific).
10. Pulse period: (the amount of time between the start of one pulse to the start of the next pulse; it includes phase duration, intrapulse intervals, and interpulse intervals) may be less than about 10 µs; or more than about 1 µs; or most desirably about 5 µs.

Figure 12:
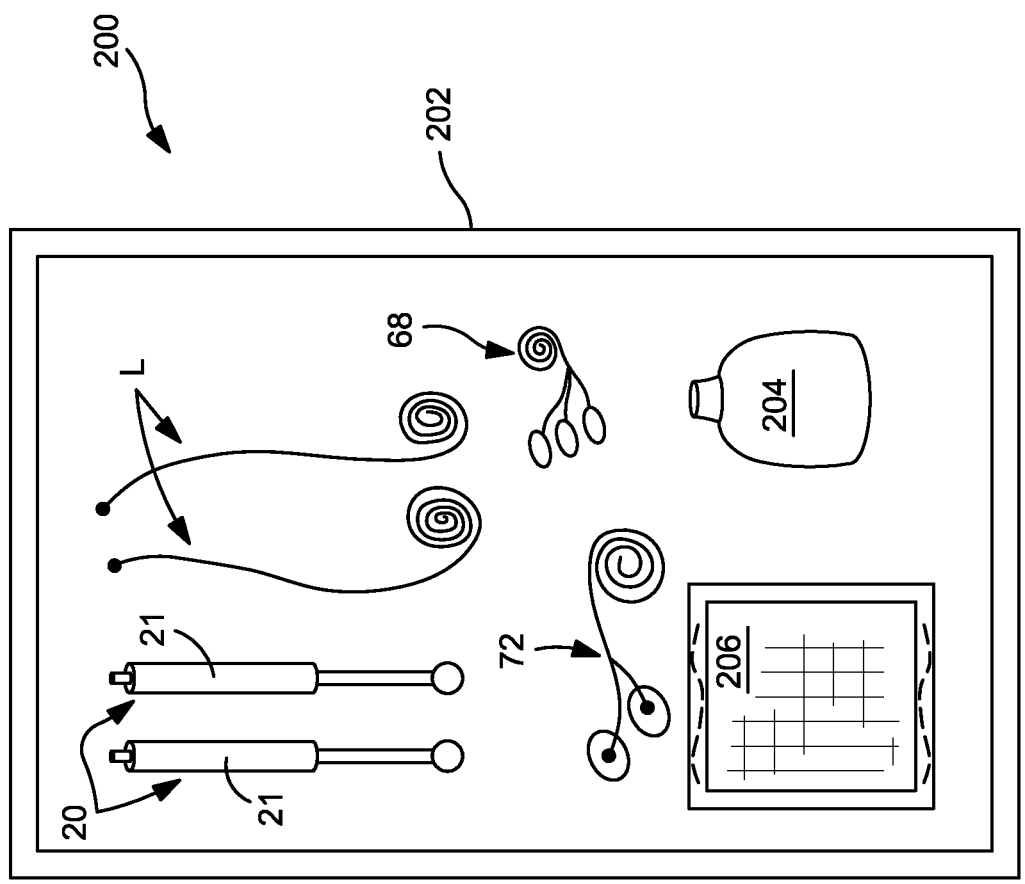
FIG. 12 is a top view of an exemplary medical procedure kit which may be used for delivering electrical stimulation to a target nerve in order to selectively block nerve fiber activity.

The present invention also encompasses a kit for an electrical nerve block procedure. FIG. 12 is meant to depict a kit 200 that includes any manner of suitable container 202 in which is provided any combination of the components depicted in FIGS. 1 through 11. It should be appreciated that the kit 200 need not contain all of the articles depicted in FIGS. 1 through 11. That is, components such as controller, pulse generator, user interface, patient monitoring system, amplifiers or the like need not be included—although suitable electrodes such as the ECG and EMG electrodes may be included in the kit.

The container 202 may be, for example, a suitable tray having a removable sealed covering in which the articles are contained. For example, an embodiment of the kit 200 may include the container 202 with one or more electrodes 20 (e.g., transcutaneous electrodes 21 are shown but percutaneous electrodes and/or nerve cuff electrodes may be contained in the kit) and electrical leads "L" as discussed above. The kit may further include one or more anodes. Each anode desirably has a skin contacting surface that has at least the same (or greater) surface area as the skin contacting surface of the stimulating electrode.

The invention encompasses a kit with any combination of the items utilized to perform the procedure of delivering electrical stimulation utilizing percutaneous electrodes described herein, utilizing nerve cuffs described here, or utilizing transcutaneous electrodes described herein. For example, other embodiments of a kit 200 may include additional items, such as ECG electrodes 68 and EMG electrodes 72, as well as any combination of a drape, site dressings, tape, skin-markers and so forth. The kit 200 may include one or more containers 204 of electrically conductive liquids or gels, antiseptics, or skin-prep liquids. The kit 200 may include pre-packaged wipes 206 such as electrically conductive liquid or gel wipes, antiseptic wipes, or skin-prep wipes. The kit may contain medicinal liquids and/or electrolytic solutions. For example, the electrolytic solution may be or may include a bioresorbable gel material that is injected in liquid form but becomes substantially viscous or even solid-like after exiting the openings in the percutaneous electrode.

Electrical Stimulation Method

The present invention also encompasses a method for selectively blocking nerve fiber activity in a target nerve.

For example—with respect to C-fibers, the method involves the steps of: locating a target nerve; positioning one or more electrodes on the skin over the target nerve, through the skin near the target nerve, or through the skin and directly on or around the nerve using the electrode assembly (e.g., including a nerve cuff or collar or a probe); and delivering electrical stimulation to the target nerve at a frequency greater than about 30 kilohertz to block nerve signal transmission of C-fibers in the target nerve such that the nerve signal transmission of the A-fibers in the target nerve providing motor function and/or low-threshold sensory function is not blocked.

In its simplest form, the method may rely on a patient's (e.g., the user) feedback of pain during delivery of nerve blocking stimulation to assess the effectiveness of the selective nerve block. Alternatively and/or additionally, the method may rely on feedback collected by a recording electrode, such as the exemplary recording electrode described above, and/or electromyogram signals to assess the effectiveness of the selective nerve block. In an aspect of the invention, the step of delivering electrical stimulation to the target nerve involves first delivering electrical stimulation to the target nerve to block nerve signal transmission of both A-fibers and C-fibers in the target nerve and then reducing the amplitude of the electrical stimulation (desirably, while maintaining or increasing the frequency of the electrical stimulation) so nerve signal transmission of the C-fibers in the target nerve is blocked and so the nerve signal transmission of the A-fibers in the target nerve providing motor function and/or low-threshold sensory function is not blocked.

In practicing the method, the electrical nerve-blocking stimulation may be high-frequency simulation, low-frequency stimulation and moderate-frequency stimulation, and combinations thereof depending on the specific nerve fiber activity to be blocked. In order to selectively block the nerve fiber activity of the C-fibers in the target nerve, the electrical nerve-blocking stimulation frequency is desirably greater than 30 kHz (e.g., from about 30 kHz to about 100 kHz), desirably less than about 25 milliamps for transcutaneous stimulation and less than about 10 milliamps for stimulation directly in the vicinity of the nerve, and is an alternating current that may be selected from sinusoidal, square-wave pulses, and a pulse train that varies in amplitude and frequency within the identified parameters (e.g., greater than 30 kHz and less than 25 mA or 10 mA). In an aspect of the invention where the nerve-blocking stimulation is applied transcutaneously, the electrical nerve-blocking stimulation may further include a carrier frequency that is greater than the stimulating frequency and the carrier frequency may range from about 100 kHz to about 1 MHz; desirably from 200 kHz to about 1 MHz.

With respect to selectively blocking nerve fiber activity in A-fibers, the method involves the steps of: locating a target nerve; positioning one or more stimulating electrodes on the skin over the target nerve or directly on or around the nerve; and delivering electrical nerve-blocking stimulation to the target nerve to block nerve signal transmission of A-fibers in the target nerve providing motor function and/or low-threshold sensory function is blocked and so that the nerve signal transmission of the C-fibers in the target nerve is not blocked.

In its simplest form, the method may rely on a patient's (e.g., the user) feedback of motor function and/or low-threshold sensory function during delivery of nerve blocking stimulation to assess the effectiveness of the selective nerve block. Alternatively and/or additionally, the method may rely on feedback collected by a recording electrode, such as the exemplary recording electrode described above, and/or electromyogram signals to assess the effectiveness of the selective nerve block. In an aspect of the invention, the step of delivering electrical nerve-blocking stimulation to the target nerve involves first delivering electrical nerve-blocking stimulation to the target nerve at a frequency to block nerve signal transmission of both A-fibers and C-fibers in the target nerve and then reducing the frequency of the electrical nerve-blocking stimulation so nerve signal transmission of the A-fibers in the target nerve providing motor function and/or low-threshold sensory function is blocked and so the nerve signal transmission of the C-fibers in the target nerve is not blocked.

In practicing the method to selectively block the nerve fiber activity of the A-fibers in the target nerve, the electrical nerve-blocking stimulation frequency is desirably less than 30 kHz (e.g., from less than about 30 kHz down to about 5 kHz), and the amplitude is desirably less than about 25 milliamps for transcutaneous stimulation and less than about 10 milliamps for stimulation directly in the vicinity of the nerve (e.g., from less than about 25 mA or 10 mA down to about 0.5 mA or even lower). The nerve blocking stimulation is desirably an alternating current that may be selected from sinusoidal, square-wave pulses, and a pulse train that varies in amplitude and frequency within the identified parameters (e.g., less than 30 kHz and less than 25 mA or 10 mA—depending on whether stimulation is transcutaneous or directly in the vicinity of the nerve). In an aspect of the invention where the nerve-blocking stimulation is applied transcutaneously, the electrical nerve-blocking stimulation may further include a carrier frequency that is greater than the stimulating frequency and the carrier frequency may range from about 100 kHz to about 1 MHz; desirably from 200 kHz to about 1 MHz.

Where the method of the invention is practiced transcutaneously, it may further include positioning one or more anodes on the skin. Each anode desirably has a skin contacting surface such that the skin contacting surface of the anode has at least the same (or greater) surface area as the skin contacting surface of the stimulating electrode. Desirably, one or more anodes are positioned on the skin over the target nerve and a distance away from one or more stimulating electrodes sufficient to avoid shunting.

Generally speaking, the use of current regulated stimuli has an advantage over voltage regulated stimuli in the transcutaneous method of the invention because the current density is better controlled.

The method of practicing the present invention may further include the use of coupling media such as, for example, an electrically conductive liquid, gel or paste that may be applied to the skin to enhance the conductivity of the skin and/or lower impedance. Alternatively and/or additionally, one or more skin moisturizers, humectants or the like may be applied to the skin for the purpose of enhancing the conductivity of the skin and/or lowering impedance of the skin. Examples of conductive pastes include Ten20™ conductive paste from Weaver and Company, Aurora, Colo., and ELEFIX Conductive Paste from Nihon Kohden with offices at Foothill Ranch, Calif. Examples of conductive gels include Spectra 360 Electrode Gel from Parker Laboratories, Inc., Fairfield, N.J. or Electro-Gel from Electro-Cap International, Inc., Eaton, Ohio.

Electrical Nerve-Blocking Stimulation
1. Setup stimulation system near a stable patient bed.
2. Place patient into a comfortable supine position.
3. Place the optional ECG and EMG on patient.
4. Begin monitoring heart-rate and EMG.
5. Locate the target nerve, either by utilizing a nerve locator (e.g., Ambu® Ministim® nerve stimulator & locator), or by passing low-levels of stimulation through the stimulator that is used for blocking. A stimulus-elicited muscle twitch in a distal muscle group with low-stimulation amplitudes (single pulse) will indicate that your stimulation point is proximal enough for blocking.
6. Position the tip of the blocking electrode in the vicinity of the nerve (or overtop of the nerve and press it gently towards the skin, decreasing the distance between the electrode and target nerve, and assuring good contact between the electrode and skin). Maintain the stimulation electrode in this position.
7. Apply electrical stimulation to the subject using the stimulating parameters described herein to selectively block nerve signal transmission in the target nerve. If a carrier signal is to be used, then determine the optimal carrier signal before blocking the nerve.

The present invention may be better understood by reference to the following examples.

Example 1

Figure 16:
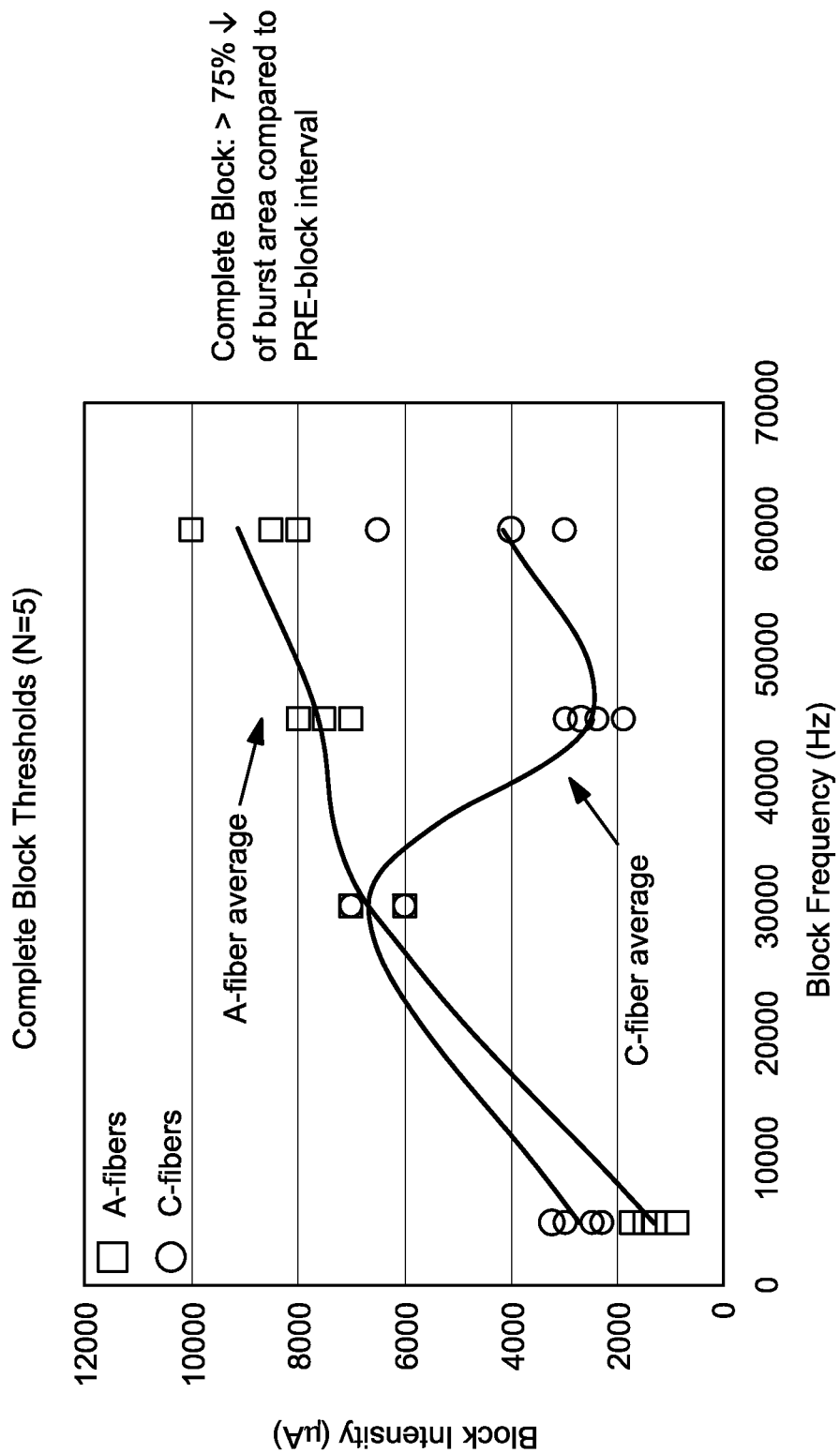
FIG. 16 is a graph showing the effectiveness of various nerve block frequencies on A-fibers and C-fibers, where the nerve block stimulation was delivered via a cuff electrode, as described in Example 1.

A nerve cuff was implanted around a target nerve and electrical stimulation was delivered to the target nerve at varying frequencies to determine the parameters to completely block A-fibers and to completely block C-fibers over a sample size of n=5. A complete block was defined as a greater than 75% decrease of burst area compared to pre-block conditions. The results are summarized in FIG. 16. As shown, nerve block stimulation frequencies of about 30,000 Hz or greater, such as between about 30,000 Hz and 70,000 Hz, resulted in the selective blocking of C-fibers with less stimulation intensity than the A-fibers, such as between about 2000 and 7000 microAmps.

Example 2

Next, the ability to selectively block C-fibers (pain fibers) in mammals with a percutaneous electrode was demonstrated, as described below.

Recordings:

Electromyography signals (EMG) were recorded unilaterally from the biceps femoris muscle with insulated and braided 13 millimeter (mm) sub-dermal needle electrodes (RhythmLink, SC). Signals were passed through a nearby headstage, bandpass filtered (500 Hz to 5000 Hz) and amplified (500×; LP511, Grass Technologies, RI), and sent to a data acquisition system (Power3 1401, Cambridge Electronic Design, UK) for digitization.

Stimulation:

Electrical stimulation was delivered through subcutaneous needle electrodes that were inserted into the subject's left foot. The tip of the cathodic stimulating electrode was placed on the foot's midline and the anode was inserted laterally. Constant-voltage, monophasic square-wave pulses (2.5 millisecond pulse duration; 0.15 Hz) were delivered at intensities sufficient to cause a brisk plantar-going twitch without causing neural windup (30 V to 150 V).

Electrical Nerve Block:

A tripolar electrode was placed percutaneously onto the sural nerve located in the lower shank. The center electrode (2 mm width) was considered to be cathodic at stimulation onset, and was flanked by 2 anodes (each anode was 2 mm width). The electrodes were made from platinum, and their inter-electrode spacing was 3 mm. The block was composed of a constant-current, charge-balanced sinusoidal stimulation delivered at various frequencies (10, 45, 51 and 61 kHz). The blocking intensities were varied during the study (<30 milliAmps).

Protocol:

Electrical stimulation was used to elicit bursts of EMG, better known as compound muscle action potentials (CMAP). The CMAPs were hosted by spinal reflexes and driven by low-threshold cutaneous sensory and nociceptive activation. The blocking electrode was placed on the sural nerve interposed between the electrodes used for sensory stimulation and recording. Multiple trials were delivered for each subject and were 120 seconds in duration. The block was centered in each trial and lasted 60 seconds. The blocking intensity was increased until visual inspection of the EMG burst caused cessation of neural activity. Lastly, the motor-threshold was determined before and after experimentation to investigate block safety.

Analysis:

Each trial was split into four 30 second epochs. The acquired data tracings were modified to approximate a leaky integrator (DC-Offset; full-wave rectified, smoothed). Spike2 (Version 8.1; Cambridge Electronic Design, UK) software was used for data processing. The area beneath the resulting EMG contour (aka: neurogram) was calculated for each electrical stimulation delivered during the trial. The sensory fiber activation types were differentiated by time post-stimulation: activation of A-fibers and C-fibers occurred between 4.5 to 45 milliseconds and 80 to 450 milliseconds post-stimulation, respectively. The areas collected during trial epochs 2-4 were compared to those collected pre-block (epoch 1).

Figure 17:
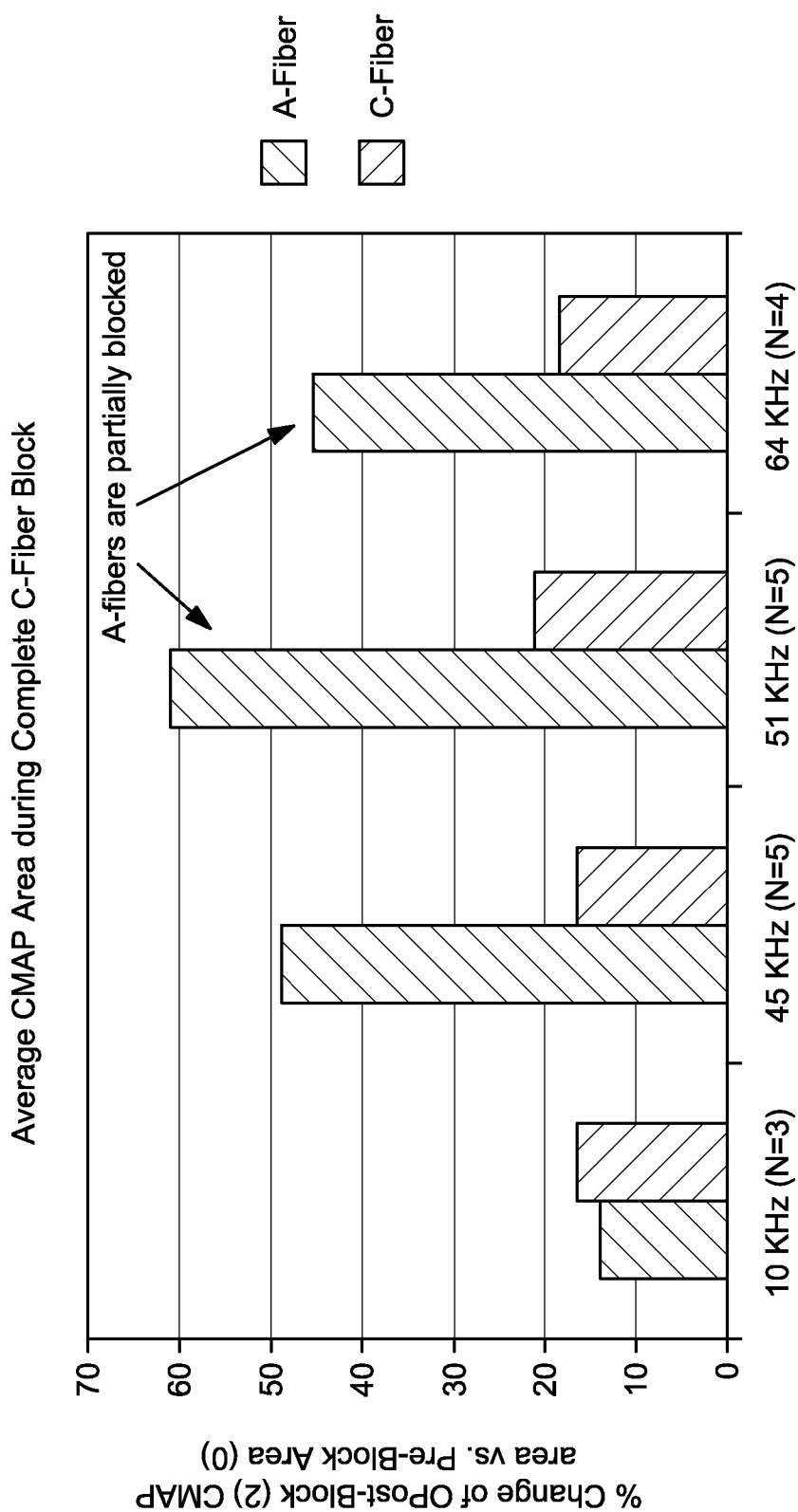
FIG. 17 is a graph showing the effectiveness of various nerve block frequencies on A-fibers and C-fibers, where the nerve block stimulation was delivered percutaneously via a probe as described in Example 2.

Results:

These data suggest that selective blocking can indeed be accomplished by electrical stimulation delivered in a percutaneous fashion. The tracings demonstrate the preservation of A-fiber activity, and a complete abolishment of C-fiber activity. FIG. 17 shows the average Compound CMAP areas collected during complete block of the C-fibers. The bar graph demonstrates that a percutaneous block delivered at 45 KHz, 51 KHz and 60 KHz disrupts the transmission of action potentials along C-fibers more than potentials carried by A-fibers. At 51 KHz, the block attenuated A-fiber activity by 40%, and C-fiber activity by 80%. Blocks delivered at 10 KHz did not demonstrate selective blocking. Motor-thresholds collected before (Average: 1.5 V; Range: 1.3 to 1.7 V) and after (Average: 1.4; Range: 1.2 V to 2 V) delivery of the various blocking trials suggest that the nerve was not damaged during testing.

Example 3

Next, the effect of the position and orientation of the percutaneous electrode utilized in Example 2 on the ability to selectively nerve block A-fibers and C-fibers was demonstrated. As shown in Table 1 below, when the uninsulated portion of the percutaneous electrode was placed directly on top of the nerve to be blocked and a 10.8 milliAmp intensity stimulation was applied at 51 kHz, the A-fibers and C-fibers were blocked, as evidenced by a decrease in nerve signal transmission from full (100%) transmission to 18.30% for the A-fibers and 7.54% for the C-fibers for the first block, and to 23.03% for the A-fibers and 6.57% for the C-fibers for the second block. Then, when the blocking stimulation was stopped, the nerve signal transmission returned to pre-block levels for both the A-fibers and the C-fibers. In contrast, when the insulated (non-active) portion of the percutaneous electrode was placed directly on top of the nerve to be blocked (i.e., the insulated, active portion was positioned 180° from the nerve) and a 11.5 milliAmp intensity stimulation was applied at 51 kHz, the A-fibers and C-fibers were not blocked, as evidenced by the minimal increase in nerve signal transmission from full (100%) transmission to 88.57% for the A-fibers and 101.32% for the C-fibers for the first block, and to 97.24% for the A-fibers and 88.54% for the C-fibers for the second block. Thus, Example 3 demonstrates the importance of minimizing movement or migration of the percutaneous electrode, where the noninsulated, active portion of the electrode should be in contact with the nerve to be blocked to facilitate effective blocking.

TABLE 1

Importance of Percutaneous Electrode Position and Orientation

Uninsulated Portion of Electrode Placed Directly on Top of Nerve

| Stimulation Intensity | Time Interval | A-Fiber Activity (%) | C-Fiber Activity (%) |
|---|---|---|---|
| 10.8 milliAmps (Peak to Peak) 51 kHz | Pre-Block | 100.00 | 100.00 |
| | Block 1 | 18.30 | 7.54 |
| | Block 2 | 23.03 | 6.57 |
| | Post-Block | 110.33 | 117.11 |

TABLE 1-continued

Importance of Percutaneous Electrode Position and Orientation

Uninsulated Portion of Electrode Turned 180° Away from Nerve

| Stimulation Intensity | Time Interval | A-Fiber Activity (%) | C-Fiber Activity (%) |
|---|---|---|---|
| 11.5 milliAmps (Peak to Peak) 51 kHz | Pre-Block | 100.00 | 100.00 |
| | Block 1 | 88.57 | 101.32 |
| | Block 2 | 97.24 | 88.54 |
| | Post-Block | 97.07 | 114.04 |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A system for selectively blocking nerve fiber activity of a peripheral nerve, the system comprising:
    an electrode assembly including one or more percutaneous electrodes each having uninsulated portions, the electrode assembly in the form of a paddle, cylindrical catheter or needle, wire form, or thin probe, the electrode assembly adapted to be introduced percutaneously through the skin, the uninsulated portion of each of the electrodes adapted to be positioned longitudinally along a long-axis of a peripheral nerve; and
    an electronic control system electrically attached to each electrode, the electronic control system configured for:
        delivering electrical stimulation to the peripheral nerve of a patient at an initial frequency and an initial amplitude to block nerve signal transmission of both A-fiber and C-fibers in the peripheral nerve;
        adjusting the delivered electrical stimulation by: i) maintaining or increasing a frequency of the delivered electrical stimulation with respect to the initial frequency, and ii) reducing an amplitude of the delivered electrical stimulation with respect to the initial amplitude;
    while adjusting the delivered electrical stimulation, monitoring patient feedback of at least one of pain, motor function, or low-threshold sensory function to determine an operating frequency and an operating amplitude that blocks nerve signal transmission in only the C-fibers of the peripheral nerve while allowing nerve signal transmission in the A-fibers of the peripheral nerve, the A-fibers providing at least one of motor function or low-threshold sensor function; and
        continuing to deliver the electrical stimulation at the determined operating frequency and operating amplitude to continuously block nerve signal transmission in only the C-fibers of the peripheral nerve;
    wherein each of the one or more percutaneous electrodes includes the uninsulated portions separated from one another along a length direction, and the uninsulated portions comprises a set of three uninsulated portions consisting of a center portion which serves as an electrode having a first uninsulated portion and two outer portions which flank the center portion and serve as electrodes having a second uninsulated portion different from the first uninsulated portion.

2. The system of claim 1, wherein the one or more percutaneous electrodes are in the form of a paddle comprising a nerve cuff, the one or more percutaneous electrodes including a blocking electrode adapted to be located in contact with the peripheral nerve.

3. The system of claim 1, wherein the one or more percutaneous electrodes are adapted to be positioned not in contact with the peripheral nerve during delivery of the electrical nerve-blocking stimulation.

4. The system of claim 3, wherein at least one of the one or more electrodes is circumferential in shape and has a diameter ranging from 0.25 mm to 10 mm.

5. The system of claim 3, wherein the electronic control system provides electrical stimulation that further includes a carrier frequency ranging from 5 kilohertz to 1 megahertz and the carrier frequency is greater than the frequency of the electrical stimulation used to block nerve signal transmission.

6. The system of claim 1, wherein the at least one of the operating frequency or the operating amplitude is further determined based on at least one of:
(i) monitoring feedback collected by a recording electrode; and
(ii) monitoring electromyogram signals.

7. The system of claim 1, wherein the operating amplitude of the electrical stimulation ranges from 2.5 mA to 10 mA.

8. The method of claim 1, wherein the operating amplitude of the electrical stimulation ranges from 2.5 mA to 15 mA.

9. The system of claim 1, wherein the operating amplitude of the electrical stimulation ranges from 2.5 mA to 5 mA.

10. The system of claim 1, wherein at least one of the one or more electrodes has a diameter ranging from 0.25 mm to 10 mm.

11. The system of claim 10, including at least two electrodes having the same polarity.

12. The system of claim 10, including at least two electrodes each having a different polarity.

13. The system of claim 1, wherein the one or more percutaneous electrodes include a cylindrical catheter or needle, wire form, or thin probe, and wherein at least one of the one or more percutaneous electrodes are a multipolar electrode including a cathode positioned along an elongated cylindrical body portion of the electrode, and an anode spaced from the cathode along the body portion of the electrode, the cathode and anode disposed radially at a surface of the electrode.

14. The system of claim 1, wherein the electrical stimulation comprises a sinusoidal waveform, the operating amplitude ranging between 2.5 mA and 20 mA and the operating frequency ranging between 30 kHz and 60 kHz.

15. A method for selectively blocking nerve fiber activity of a peripheral nerve, the method comprising:
positioning an electrode adjacent and longitudinally along a long-axis of a peripheral nerve of a patient, the electrode adapted for introduction percutaneously through the skin and be positioned longitudinally along a long-axis of the target peripheral nerve, the electrode including uninsulated portions, each of the uninsulated portions separated from one another along a length direction, and the uninsulated portions comprising a set of three uninsulated portions consisting of a center portion which serves as an electrode having a first uninsulated portion and two outer portions which flank the center portion and serve as electrodes having a second uninsulated portion different from the first uninsulated portion;

delivering electrical stimulation to the peripheral nerve at an initial frequency and an initial amplitude to block nerve signal transmission of both A-fibers and C-fibers in the peripheral nerve;
adjusting the delivered electrical stimulation by: i) maintaining or increasing a frequency of the delivered electrical stimulation with respect to the initial frequency, and ii) reducing an amplitude of the delivered electrical stimulation with respect to the initial amplitude;
while adjusting the delivered electrical stimulation, monitoring patient feedback of at least one of pain, motor function, or low-threshold sensory function to determine an operating frequency and an operating amplitude that blocks nerve signal transmission in only the C-fibers of the peripheral nerve while allowing nerve signal transmission in the A-fibers of the peripheral nerve, the A-fibers providing at least one of motor function or low-threshold sensor function; and
continuing to deliver the electrical stimulation at the determined operating frequency and operating amplitude to continuously block nerve signal transmission in only the C-fibers of the peripheral nerve.

16. The method of claim 15, wherein the electrode is a blocking electrode positioned on a cuff to contact the peripheral nerve.

17. The method of claim 15, wherein the electrode is not required to contact the peripheral nerve during delivery of the electrical stimulation and wherein the electrical stimulation comprises a sinusoidal waveform having an amplitude ranging between 2.5 mA and 20 mA and a frequency ranging between 30 kHz and 60 kHz.

18. The method of claim 15, wherein the electrical stimulation further includes a carrier frequency ranging from 5 kilohertz to 1 megahertz and the carrier frequency is greater than the frequency of the electrical stimulation.

19. The method of claim 15, further comprising the step of applying a local anesthetic to the peripheral nerve prior to delivering the electrical stimulation, the local anesthetic being applied in an amount sufficient to relieve an onset response in connection with the delivery of the electrical stimulation.

20. The method of claim 15, wherein the at least one of the operating frequency or the operating amplitude is further determined based on at least one of:
(i) monitoring feedback collected by a recording electrode; and
(ii) monitoring electromyogram signals.

21. A system for selectively blocking block of nerve fiber activity of a peripheral nerve, the system comprising:
one or more electrodes adapted to be introduced percutaneously though the skin and positioned in contact with and longitudinally along a long-axis of a peripheral nerve; and
an electronic control system electrically attached to each of the one or more electrodes, the electronic control system configured for:
delivering electrical stimulation to the peripheral nerve of a mammal at an initial frequency to block nerve signal transmission of both A-fibers and C-fibers in the peripheral nerve,
adjusting the delivered electrical stimulation by reducing a frequency of the delivered electrical stimulation with respect to the initial frequency;
while adjusting the delivered electrical stimulation, monitoring patient feedback of at least one of pain, motor function, or low-threshold sensory function to determine an operating frequency that blocks nerve signal transmission in only the A-fibers of the peripheral nerve while allowing nerve signal transmission in the C-fibers of the peripheral nerve, the A-fibers providing at least one of motor function or low-threshold sensor function; and continuing to deliver the electrical stimulation at the determined operating frequency to continuously block nerve signal transmission in only the A-fibers of the peripheral nerve;

wherein each of the one or more electrodes includes uninsulated portions, the uninsulated portions separated from one another along a length direction, and the uninsulated portions comprises a set of three uninsulated portions consisting of a center portion which serves as an electrode having a first uninsulated portion and two outer portions which flank the center portion and serve as electrodes having a second uninsulated portion different from the first uninsulated portion.

22. The system of claim 21, wherein the electrical stimulation comprises a sinusoidal waveform having an amplitude less than 25 mA and a frequency less than 30 kHz.

23. The system of claim 21, wherein the one or more electrodes comprise a nerve cuff, paddle, cylindrical catheter or needle, wire form, or thin probe, wherein when the electrode assembly is in the form of a nerve cuff the one or more electrodes comprise a blocking electrode located on the nerve cuff adapted to contact the peripheral nerve.

24. The system of claim 21, wherein the electronic control system provides electrical stimulation that further includes a carrier frequency ranging from 5 kilohertz to 1 megahertz and the carrier frequency is greater than the frequency of the electrical stimulation used to block nerve signal transmission.

25. A method for selectively blocking nerve fiber activity of a peripheral nerve, the method comprising:

positioning an electrode in contact with and longitudinally along a long-axis of a peripheral nerve of a patient, the electrode adapted for introduction percutaneously through the skin and be positioned longitudinally along the long-axis of the peripheral nerve, the electrode including uninsulated portions, each of the uninsulated portions separated from one another along a length direction, and the uninsulated portions comprising a set of three uninsulated portions consisting of a center portion which serves as an electrode having a first uninsulated portion and two outer portions which flank the center portion and serve as electrodes having a second uninsulated portion different from the first uninsulated portion;

delivering electrical stimulation to the peripheral nerve at an initial frequency to block nerve signal transmission of both A-fibers and C-fibers in the peripheral nerve adjusting the delivered electrical stimulation by reducing a frequency of the delivered electrical stimulation with respect to the initial frequency;

while adjusting the delivered electrical stimulation, monitoring patient feedback of at least one of pain, motor function, or low-threshold sensory function to determine at least one of an operating frequency that blocks nerve signal transmission in only the A-fibers of the peripheral nerve while allowing nerve signal transmission in the C-fibers of the peripheral nerve, the A-fibers providing at least one of motor function or low-threshold sensor function; and continuing to deliver the electrical stimulation at the determined operating frequency to continuously block nerve signal transmission in only the A-fibers of the peripheral nerve.

26. The method of claim 25, wherein the electrode comprises a blocking electrode located on a cuff adapted to contact the peripheral nerve.

27. The method of claim 25, wherein the electrode includes a paddle, cylindrical catheter or needle, wire form, or thin probe, configured to be introduced percutaneously through the skin and wherein the electrical stimulation comprises a sinusoidal waveform having an amplitude less than 25 mA, and a frequency less than 30 kHz.

28. The method of claim 27, wherein the electrical stimulation further includes a carrier frequency ranging from 5 kilohertz to 1 megahertz and the carrier frequency is greater than the frequency of the electrical stimulation used to block nerve signal transmission.

29. The method of claim 25, further comprising the step of applying a local anesthetic to the peripheral nerve prior to delivering the electrical stimulation, the local anesthetic being applied in an amount sufficient to relieve an onset response in connection with the delivery of electrical stimulation.

30. The method of claim 25, wherein the electrical stimulation further includes a carrier frequency ranging from 5 kilohertz to 1 megahertz and the carrier frequency is greater than the frequency of the electrical stimulation used to block nerve signal transmission.

* * * * *